United States Patent
Carr et al.

(10) Patent No.: US 11,319,976 B2
(45) Date of Patent: *May 3, 2022

(54) INTEGRATED BELT AND SENSOR FOR ALARM FOR PATIENT FURNITURE

(71) Applicant: TIDI Products, LLC, Neenah, WI (US)

(72) Inventors: Roy Seizo Carr, Fontana, CA (US);
Alex Bekker, Sherman Oaks, CA (US);
Samantha McCarthy, Libertyville, IL (US); Shayna Massi, Palatine, IL (US);
Beth Hudson, Chicago, IL (US);
Brittany Johnson, Salem, WI (US)

(73) Assignee: TIDI Products, LLC, Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/088,277

(22) Filed: Nov. 3, 2020

(65) Prior Publication Data

US 2021/0048051 A1 Feb. 18, 2021

Related U.S. Application Data

(63) Continuation of application No. 16/443,389, filed on Jun. 17, 2019, now abandoned, which is a
(Continued)

(51) Int. Cl.
*F16B 2/08* (2006.01)
*A41F 9/00* (2006.01)
(Continued)

(52) U.S. Cl.
CPC .................. *F16B 2/08* (2013.01); *A41F 9/00* (2013.01); *A41F 9/002* (2013.01); *F16B 2/00* (2013.01); *G08B 21/18* (2013.01)

(58) Field of Classification Search
CPC ... A61B 5/1115; A61B 5/1117; A61B 5/1126; A41F 9/002; Y01T 24/141;
(Continued)

(56) References Cited

U.S. PATENT DOCUMENTS 4,417,572 A 11/1983 Green
4,777,944 A * 10/1988 Green .................. A61F 5/3784
128/874

(Continued)

FOREIGN PATENT DOCUMENTS

CN 105361347 A 3/2016
CN 205729594 U 11/2016
(Continued)

OTHER PUBLICATIONS

Search Report for PCT Patent Application No. PCT/US2020/038080, "Integrated Belt and Sensor for Alarm for Patient Furniture" dated Sep. 3, 2020.
(Continued)

*Primary Examiner* — Van T Trieu
(74) *Attorney, Agent, or Firm* — Davis & Kuelthau, s.c.

(57) ABSTRACT

Systems and methods for monitoring the location of a patient using an integrated belt and sensor for alarm for patient furniture. The belt may include a plurality of straps configured to be releasably attached to one another and an alarm system that is triggered when at least one of the straps is disengaged from the other strap or straps. By requiring multiple straps to be released from one another, the amount of time it takes to remove the belt can be increased, which provides medical personnel additional time to reach a patient. Additionally, the system may include additional components to allow a patient to move side-to-side relative to the furniture or device. For instance, where the furniture is a bed, side-to-side movement is desired for added com-
(Continued)

fort. The system may include a slider enabling the belt to be adjustable for patients of any number of different sizes.

19 Claims, 26 Drawing Sheets

Related U.S. Application Data continuation-in-part of application No. 16/054,183, filed on Aug. 3, 2018, now Pat. No. 10,321,854.

(60) Provisional application No. 62/540,879, filed on Aug. 3, 2017.

(51) Int. Cl.
*F16B 2/00* (2006.01)
*G08B 21/18* (2006.01)

(58) Field of Classification Search
CPC ............. Y01T 24/1418; Y01T 24/1469; Y01T 24/148; Y01T 24/21; F16B 17/00; F16B 17/004; F16B 17/006; F16B 17/008; F16B 13/00; F16B 13/002; F16B 13/009; F16B 13/02; F16B 13/025; F16B 2/00; F16B 2/08; B65B 1/00; B65B 1/002; B65B 1/006; B65B 1/008
See application file for complete search history.

(56) References Cited

U.S. PATENT DOCUMENTS

| | | |
|---|---|---|
| 5,076,288 A | 12/1991 | Millard et al. |
| 5,161,545 A | 11/1992 | McCarthy |
| 5,494,046 A | 2/1996 | Cross |
| 5,844,488 A | 12/1998 | Musick |
| D404,845 S | 1/1999 | McIntyre et al. |
| 6,078,261 A | 6/2000 | Davsko |
| 6,085,154 A | 7/2000 | Leuthausser et al. |
| 6,311,374 B1 | 11/2001 | Anscher |
| 6,557,557 B2 | 5/2003 | Hamama |
| 6,778,090 B2 | 8/2004 | Newham |
| 6,796,007 B1 | 9/2004 | Anscher |
| 6,917,293 B2 | 7/2005 | Beggs |
| 7,282,031 B2 | 10/2007 | Hendrich |
| 7,319,400 B2 | 1/2008 | Smith et al. |
| 7,420,472 B2 | 9/2008 | Tran |
| 7,682,308 B2 | 3/2010 | Hendrich |
| 7,836,529 B2 | 11/2010 | Cherubini et al. |
| 7,916,036 B1 | 3/2011 | Pope et al. |
| 7,924,163 B1 | 4/2011 | Long |
| 7,938,121 B2 | 5/2011 | McKnight et al. |
| 8,211,014 B2 | 7/2012 | David et al. |
| D680,900 S | 4/2013 | Grimm |
| 8,449,471 B2 | 5/2013 | Tran |
| 8,451,129 B2 | 5/2013 | Hamdan |
| 8,500,636 B2 | 8/2013 | Tran |
| 8,521,490 B2 | 8/2013 | Hardigan |
| 8,529,448 B2 | 9/2013 | McNair |
| D701,139 S | 3/2014 | Kadoishi |
| 8,708,903 B2 | 4/2014 | Tran |
| 8,866,620 B2 | 10/2014 | Amir |
| D717,206 S | 11/2014 | Tannello et al. |
| 8,968,195 B2 | 3/2015 | Tran |
| 9,064,482 B2 * | 6/2015 | Henriques ............... G10H 1/344 |
| D749,462 S | 2/2016 | Paik et al. |
| 9,311,540 B2 | 4/2016 | Ecker et al. |
| 9,314,159 B2 | 4/2016 | Lyon et al. |
| 9,386,863 B1 | 7/2016 | Antunovic |
| 9,466,204 B2 | 10/2016 | Olson |
| 9,480,307 B2 | 11/2016 | Makley |
| 9,558,641 B2 | 1/2017 | Brasch et al. |
| D778,779 S | 2/2017 | Fujii |
| 10,188,296 B2 | 1/2019 | ALAli et al. |
| 10,357,197 B2 | 7/2019 | Smith et al. |
| 10,438,475 B2 | 10/2019 | Williams |
| 10,438,496 B2 | 10/2019 | Panzer |
| 2002/0068883 A1 | 6/2002 | Hamama |
| 2005/0076920 A1 | 4/2005 | Dubats |
| 2005/0080360 A1 | 4/2005 | Katz et al. |
| 2005/0150503 A1 | 7/2005 | Votel |
| 2011/0034845 A1 | 2/2011 | Polliack et al. |
| 2012/0032808 A1 | 2/2012 | Cherubini |
| 2013/0019882 A1 | 1/2013 | Durham et al. |
| 2014/0224262 A1 | 8/2014 | Parent et al. |
| 2015/0157488 A1 | 6/2015 | Grunden et al. |
| 2016/0198809 A1 * | 7/2016 | Grunden ................ A44B 11/28 602/4 |
| 2016/0307429 A1 | 10/2016 | Hood et al. |
| 2018/0168459 A1 | 6/2018 | Tran |
| 2019/0038183 A1 | 2/2019 | Carr |
| 2019/0304283 A1 | 10/2019 | Carr et al. |
| 2020/0020240 A1 | 1/2020 | Panzer |

FOREIGN PATENT DOCUMENTS

| | | |
|---|---|---|
| CN | 106999300 A | 8/2017 |
| EP | 2384726 A1 | 11/2011 |
| TW | M542454 U | 6/2017 |

OTHER PUBLICATIONS

DeRoyal Double-Lock Security Cuffs, Leather Limb Holders, and Fixed Position Cuffs, retrieved at least as early as Nov. 18, 2017; 10 pages.
E.M. Adams Company Limb Holder Application Instruction, retrieved at least as early as Nov. 16, 2017; 5 pages.
Posey Healthcare Products Guide 1996; 2 pages.
Posey Patient Safety Aids—1985 Edition—Product Catalog; 6 pages.
Posey Patient Safety Aids—1989—1990 Product Line; 4 pages.
Owner Unknown, non-patent literature search conducted by USPTO Examiner in related case with U.S. Appl. No. 17/190,167, provided by Examiner on Jan. 26, 2022.

* cited by examiner

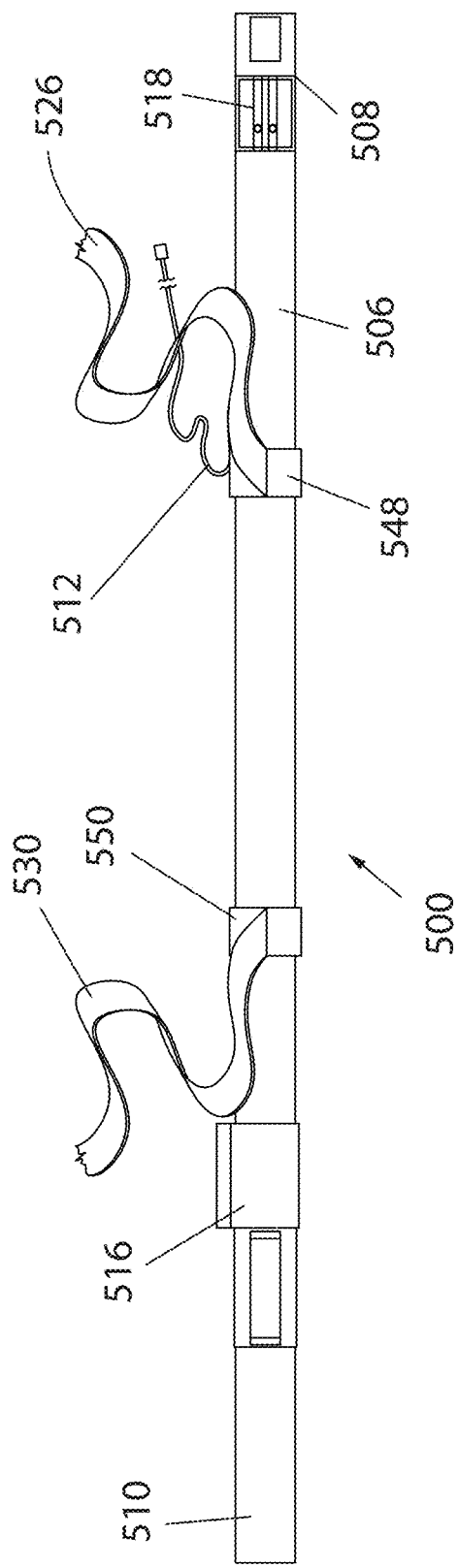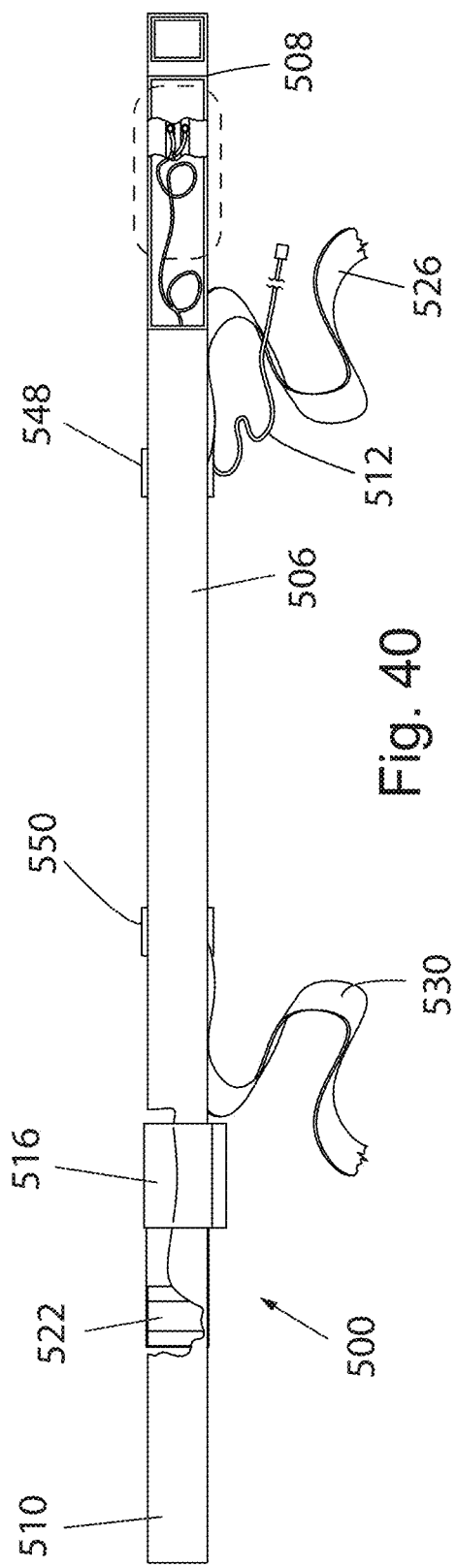

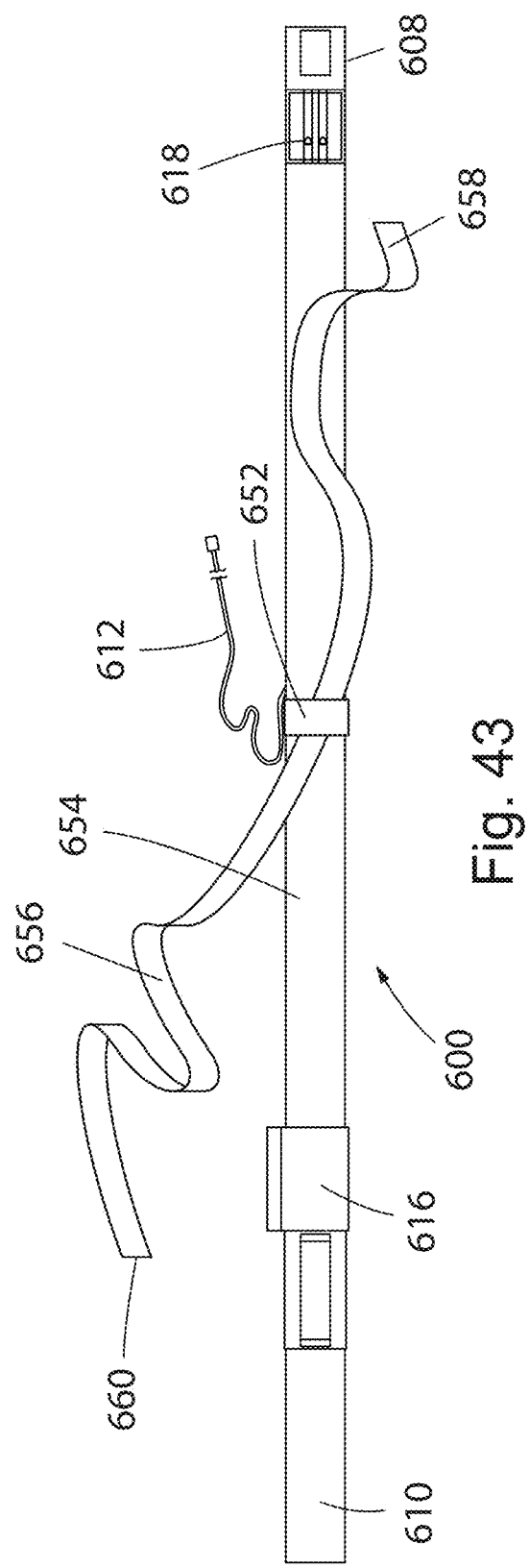
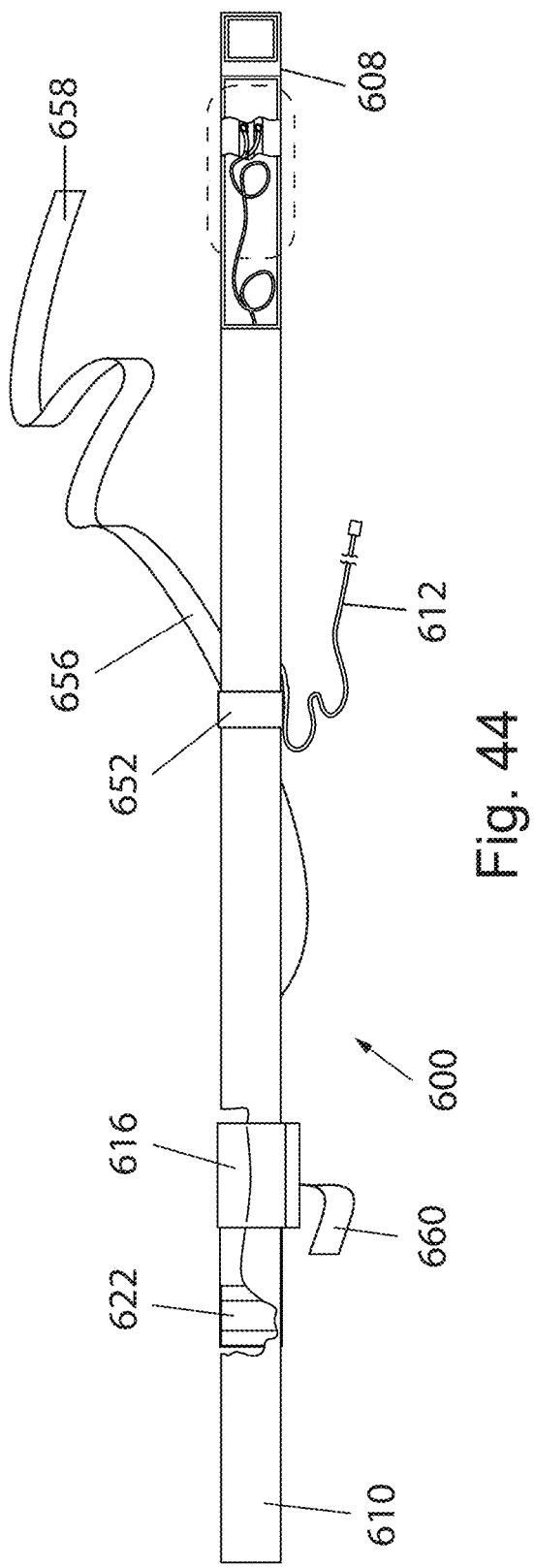

INTEGRATED BELT AND SENSOR FOR ALARM FOR PATIENT FURNITURE

CROSS-REFERENCE TO RELATED APPLICATION

This application is a continuation of U.S. Non-Provisional application Ser. No. 16/443,389, filed on Jun. 17, 2019, which is a continuation-in-part of U.S. Non-Provisional application Ser. No. 16/054,183, filed on Aug. 3, 2018, now U.S. Pat. No. 10,321,854, issued Jun. 18, 2019, which claims the benefit of U.S. Provisional Patent Application Ser. No. 62/540,879 filed on Aug. 3, 2017 and titled Predictive Double Release Alarm Belt, the entirety of which is incorporated by reference herein.

BACKGROUND OF THE INVENTION

1. Field of the Invention

The present invention relates, in general, to the field of fall prevention devices. More particularly, the present invention relates to a device that allows medical personnel to monitor the location of various patients. Specifically, a preferred embodiment of the present invention relates to a belt that can be secured about a device on which a patient sits or lays that alerts medical personnel when the belt is removed or partially removed. Additionally, a preferred embodiment of the present invention relates to a belt that allows the patient to move relative to the device on which the patient sits or lays to increase comfort, while also alerting medical personnel when the belt is removed or partially removed.

2. Discussion of the Related Art

Falls and fall-related injuries pose significant health issues, especially for elderly individuals. Incidence of falls in hospitalized patients ranges from 2.6-7.0 falls per 1,000 patient days. 23-42% of these falls result in some type of injury. To address these health issues, various fall-prevention equipment is commonly used in hospitals, assist care facilities, nursing homes, senior citizen facilities, and any other locations to protect patients and residents. For instance, various sensors, alarms, and other devices are used to monitor the location and movement of individuals. By way of example, many pieces of furniture, including chairs, beds, wheelchairs, toilets, and the like, feature sensors that alert medical personnel when an individual exits these pieces of furniture. In the event an individual stands up, the sensor can trip an alarm that alerts medical personnel. Once the alarm is sounded, appropriate attention can be given to the individual who may not be steady on his or her feet.

One such type of fall-prevention equipment relates to belts that are wrapped around a patient who is sitting in a chair or lying in a bed. In the event the individual wishes to get up from the chair or bed, he or she must disengage the belt. Once the fastener of the belt is disengaged, an alarm is sounded to alert the medical staff.

While these fall-prevention belts are helpful, further improvements are desired. For instance, current fall-prevention belts resemble traditional belts, which can be disengaged quickly and easily by simply separating the first end and the second end at a single release point. Once the first end and the second end are disengaged about the single release point such that the belt is completely separated, an alarm is sounded. As a result, once the alarm is sounded, the patient is able to immediately stand up and move around, as desired. This means that the medical personnel must act immediately, and even then, the patient may have stood up, moved, or fallen down.

Additionally, traditional fall-prevention belts are expensive, requiring them to be reused. In many settings, such as household settings, this is not an issue. However, in hospital settings, sterility concerns require extensive cleaning before a fall-prevention belt is ready to be reused. This also adds to the cost of using and maintaining fall prevention belts.

Another issue with many fall-prevention belts is that they unnecessarily restrict the patient's movements. This can cause discomfort for the patient. This is especially true in situations where a patient is in the same position for extended periods of time. For instance, when a patient is on bedrest, if a fall-prevention belt is used that unnecessarily restricts the patient's movements, the patient may experience bed sores due to prolonged contact with the bed.

What is needed, therefore, is a fall-prevention alarm belt that addresses at least the issues outlined above. More specifically, an alarm belt that provides medical personnel with additional time to reach the patient before the patient is able to stand up is needed. Similarly, an alarm belt that requires additional time for a patient to disengage is further needed. Further, what is needed is an affordable, disposable fall-prevention belt that can be installed to a chair, a bed, or another piece of furniture on which a patient is sitting or lying. Further still, what is needed is a fall-prevention belt that allows a patient to move side-to-side relative to a device such as a bed without falsely tripping the alarm.

SUMMARY AND OBJECTS OF THE INVENTION

By way of summary, the present invention is directed to a double-release alarm belt that is used with a device that holds or supports a patient. A primary object of the invention is to provide an apparatus that allows medical personnel to monitor the location of the patient relative to the device. Another object of the invention is to provide an apparatus that is affordable and disposable for industries where sterility concerns are prevalent.

In accordance with a first aspect of the invention, these objects are achieved by providing an apparatus having at least three straps, a cord configured to detect movement of at least one of the straps, and an alarm system connected to the cord. The at least three straps may be releasably secured to one another around the device and the patient. For instance, the at least three straps may include a first elongated strap, a second elongated strap releasably attached to the first elongated strap, a third elongated strap, and a fourth elongated strap releasably attached to the third elongated strap.

The at least three straps may be disengaged from the device and the patient by moving a first strap in a first direction and then moving a second strap in a second direction. Once the first strap is moved in the first direction, the cord may provide a transmission to the alarm system that results in the sounding of the alarm system. For instance, the third elongated strap may be disengaged from the fourth elongated strap by pulling the third elongated strap in the first direction. Once this occurs, the alarm system may be triggered. Thereafter, the first elongated strap may be disengaged from the second elongated strap by pulling the second elongated strap in the second direction opposite the first direction.

The apparatus may also include first, second, third, and fourth fasteners. For instance, the first fastener may be located on an upper side of the first elongated strap. The second fastener may be located on an underside of the second elongated strap, such that the second fastener is configured to releasably fasten to the first fastener. Additionally, the third fastener may be located on an underside of the third elongated strap. Finally, the fourth fastener may be located on an upper side of the fourth elongated strap, such that the first fastener is configured to releasably fasten to the third fastener. Also, a bond between the third fastener and the fourth fastener may be weaker than a bond between the first fastener and the second fastener.

Further still, the apparatus may include first and second handles. The first handle may be mounted to an upper side of the third elongated strap. This allows the third elongated strap to be disengaged from the fourth elongated strap by pulling on the first handle. The second handle may be mounted to an upper side of the second elongated strap to allow the second elongated strap to be disengaged from the first elongated strap.

In accordance with another aspect of the invention, these objects are achieved by providing an apparatus comprising an inventive double-release alarm belt with a first elongated strap, a second elongated strap, a shortened strap, a cord, and an alarm system. The first elongated strap, the second elongated strap, the shortened strap, and the cord can be disposable, or they can be reusable.

The first elongated strap may have a first end, a second end, a midportion located between the first and the second end, an upper side, and an underside. The first elongated strap may also have a hook mechanism that is attached to the first end of the first elongated strap. The hook mechanism may be used to engage a second end of the second elongated strap. More specifically, the hook mechanism may comprise a first ring and a second ring where the second end of the second elongated strap is threaded through the first ring and the second ring. Additionally, the first elongated strap may have a first fastener extending along the underside of the second end of the first elongated strap.

The shortened strap may also have a first end, a second end, an upper side, and an underside. The shortened strap may be attached to the midportion of the first elongated strap about the first end of the shortened strap. Additionally, a second fastener may extend along the upper side of the shortened strap from the first end of the shortened strap to the second end of the shortened strap.

Similarly, the second elongated strap may have a first end, a second end, an intermediate portion located between the first end and the second end, an upper side, and an underside. A third fastener may extend along the underside of the first end of the second elongated strap and a fourth fastener may extend along the upper side of the intermediate portion.

The first fastener may be releasably engaged by the fourth fastener, and the second fastener may be releasably engaged by the third fastener. More specifically, the first fastener may be releasably held together with the fourth fastener by a first bond and the second fastener may be releasably held together with the second fastener by a second bond. The first bond may be weaker than the second bond. This allows the bond between the first fastener and the fourth fastener to be easily broken. It is more difficult to break the bond between the second fastener and the third fastener. In this way, a patient can easily break the first bond, but it will be more difficult to break the second bond. Also, the first fastener is disengaged from the fourth fastener using a first force and the second fastener is disengaged from the fourth fastener using a second force. The first force is less than the second force. Each of the fasteners may be selected from one of a hook fastener and a loop fastener.

The cord is associated with the first elongated strap, the second elongated strap, and the shortened strap and is in communication with an alarm system. If the first fastener is disengaged from the fourth fastener as monitored by the cord, the alarm system will generate an audible sound. This will notify medical personnel that there is risk that the patient is preparing to leave the device before the patient is actually able to leave the device. To disengage the various fasteners, the first fastener is disengaged from the fourth fastener when the first fastener is pulled in a first direction. Next, the second fastener may be disengaged from the third fastener by pulling in a second direction, which is opposite to the first direction. By requiring the patient to pull in the first direction and then the second direction, it takes additional time to disengage the double-release alarm belt in comparison to previous belts.

The inventive double-release belt may also include a first handle that is mounted to the upper side of the second end of the first elongated strap. Thus, the first handle is used to disengage the first fastener from the fourth fastener. The double-release belt also may include a second handle mounted to the upper side of the first end of the second elongated strip. Therefore, the second handle is used to disengage the first fastener from the fourth fastener.

The double-release belt preferably may also include a fifth fastener. The fifth fastener may be associated with the second end of the second elongated strap. The fifth fastener may be used to secure the first elongated strap, the second elongated strap, and the shortened strap in a wrapped position. Additionally, the fifth fastener may be used to secure the second end of the second elongated strap to the double-release belt once installed.

In accordance with another aspect of the invention, these objects are achieved by providing a method of using the double-release alarm belt with a device holding a patient. The first step of the method is wrapping the double-release arm belt around the patient. Next, the double-release alarm belt is wrapped around the device. A first end of the double-release alarm belt is then engaged with a second end of the double-release alarm belt to secure the first and second ends to one another. Next, an alarm system is connected to the double-release alarm belt by a cord.

The method may include additional steps. The first elongated strap may be disengaged from the second elongated strap about a first portion. For instance, a first handle can be pulled to disengage the first elongated strap from the second elongated strap about a first portion. When this occurs, an audible alarm can be created by the alarm system. Additionally, the first elongated strap may be disengaged from the second elongated strap about a second portion. For instance, a second handle can be pulled to disengage the first elongated strap from the second elongated strap about a second portion. When this occurs, the patient is released so that he or she can move away from the device. Also, the first end of the double-release alarm belt may be threaded through a first ring and a second ring associated with the second end of the double-release belt. When this occurs, the belt is snug about the patient. Additionally, the first end of the double-release alarm belt can be secured in place using a hook and loop fastener.

In accordance with another aspect of the invention, a double-release alarm belt for use with a device holding a patient may include a first elongated strap, a shortened strap, a second elongated strap, and an alarm system. The shortened strap may extend from the first elongated strap. The second elongated strap may be configured to be releasably attached to the first elongated strap and to be releasably attached to the shortened strap. The alarm system is triggered when the second elongated strap is disengaged from the first elongated strap. The second elongated strap may be disengaged from the first elongated strap by pulling the first elongated strap in a first direction. The second elongated strap may also be disengaged from the shortened strap by pulling the second elongated strap in a second direction opposite the first direction.

In accordance with another aspect of the invention, an integrated belt and sensor for alarm system for use with a device holding a patient is described. The system may include at least one strap having a first end and a second end, where the first end and second end are releasably secured to one another around the patient. Additionally, the system may include a cord that is configured to detect movement of the first end relative to the second end. An alarm system is then connected to the cord. The alarm system may be activated when the first end and the second end are separated.

In accordance with yet another aspect of the invention, the at least one strap may include a first elongated strap and a second shortened strap. The second shortened strap is configured to be releasably attached to the first elongated strap. The second shortened strap may be disengaged from the first elongated strap by pulling the second shortened strap in a first direction, after which the alarm system will be triggered. The second shortened strap may be slidably adjustable relative to the first elongated strap. Additionally, the system may have multiple fasteners. For instance, the system may include a first fastener on an upper side of the first elongated strap and a second fastener on an underside of the second shortened strap. The second fastener may be configured to releasably fasten to the first fastener, and the alarm system may be triggered when the first fastener is separated from the second fastener.

In accordance with another aspect of the invention, the system may include at least one securement strap that is configured to secure the system to the device, while also allowing the patient to move side-to-side relative to the device. For instance, the system may include a first securement strap extending from the first elongated strap that is configured to be secured to the first side of the device. Additionally, the system may include a second securement strap extending from the first elongated strap that is configured to be secured to a second side of the device. The securement straps may be secured to various components associated with the system. For instance, the straps may be mounted to hooks that are slidable relative to tracks mounted to the first elongated strap. For instance, a first track may be mounted to an outer side of the first elongated strap at a first end and a second track may be mounted to the outer side of the first elongated strap at a second end. In such an embodiment, a first hoop may be mounted to the first securement strap, where the first hoop travels along the first track. Similarly, a second hoop may be mounted to the second securement strap, where the second hoop travels along the first track. In another embodiment, the securement straps are mounted to sliders that are wrapped around the first elongated strap. For instance, a first slider may be wrapped around a first end of the elongated strap and a second slider may be wrapped around a second end of the elongated strap. In such an embodiment, the first slider is configured for slidable movement along the first end and the second slider is configured for slidable movement along the second end. The first securement strap may extend from the first slider and the second securement strap may extend from the second slider. In yet another embodiment, the system may include a loop mounted on a back of the first elongated strap. A single securement strap having first and second ends may be threaded through the loop, with either side of the securement strap being fastened to either side of the device. Alternatively still, the system may include a first strap wrapped around the body of the patient, and second and third securement straps extending from opposite ends of the first strap. These securement straps may wrap around the back of the patient, for instance in a criss-cross configuration.

In yet another embodiment, the at least one strap may include a first elongated strap having a first end, a second end, a middle portion located therebetween, and an opening formed in the middle portion. The at least one strap may also include a second elongated strap that extends through the opening formed in the first elongated strap.

In accordance with yet another aspect of the invention, a method is provided. The method may include first wrapping at least one strap temporarily around the patient. When this occurs, a first end of the at least one strap is engaged with a second end of the at least one strap. An alarm system is then connected to the at least one strap. At least one securement strap that extends from the at least one patient strap is then secured to a side of the device, which in turn enables side-to-side movement of the patient relative to the device. When the first end and the second end are separated from one another, the alarm system may be enabled. After the alarm system is enabled, the system must be further disengaged before the patient can exit the device.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which:

FIG. 21 illustrates a perspective view of the inventive predictive double-release alarm belt that is mounted around a patient and a device the patient is sitting or lying on;

FIG. 22 illustrates a perspective view of the inventive predictive double-release alarm belt in a preferred position relative to the patient and a device that the patient is resting on;

FIG. 39 illustrates a front side elevation view of an inventive integrated belt and sensor for alarm for patient furniture of the present invention;

FIG. 40 illustrates a rear side elevation view of the inventive integrated belt and sensor for alarm for patient furniture of FIG. 39;

FIG. 43 illustrates a front side elevation view of an inventive integrated belt and sensor for alarm for patient furniture of the present invention;

FIG. 44 illustrates a rear side elevation view of the inventive integrated belt and sensor for alarm for patient furniture of FIG. 43;

Figure 1:
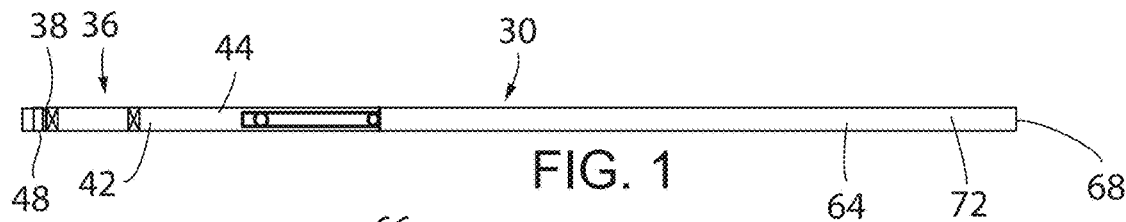
FIG. 1 illustrates a side elevation view of an inventive predictive double-release alarm belt of the present invention.

In describing the preferred embodiment of the invention, which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

1. System Overview

The current invention relates to a belt with two releasable straps portions which is connected to an alarm that can be secured around an occupant of a chair, bed, or other supporting device to monitor patient movement non-invasively. When a first releasable strap portion is disengaged by pulling in a first direction, an alarm will sound. The second releasable strap portion can then be disengaged by pulling in a second direction, which is opposite to the first direction. This gives an early warning to the medical personnel before the occupant attempts to exit the chair or bed. As a result, the necessary staff has time to intervene to assist the occupant who may be a fall risk. The belt could either be disposable or reusable based on the materials used. By offering both disposable and reusable belts, cost efficiency can be optimized depending on the specific context in which the belt is used. This invention is superior to previous sensor pads or alarms that typically only sound once the occupant has already exited the chair, bed, or other supporting device. The invention provides the earliest possible warning that a patient is at immediate risk of falling when exiting the bed, while also being non-invasive.

Additionally, the current invention may also include features that allow for increased range of motion when a patient is secured to a device, such as a piece of furniture including a bed. These features can easily be incorporated with various disposable alarmed belts, some of which have two release points that provides a health care provider with an early warning that a patient is trying to leave the furniture. This early warning can provide the provider with additional time to intervene prior to a potential fall. The invention may be made of various low-profile, soft materials to avoid potential pressure injuries. The invention may also be made of hydrophobic material and flat surfaces to simplify cleaning. Further still, the invention may be compatible with a variety of different devices and furniture. Preferably, the invention is of a simple design with minimal components to support the ease of use by end users.

2. Detailed Description of Preferred Embodiments

The inventive double-release alarm belt 30 is generally shown in the figures. The double-release alarm belt 30 is used to monitor the position of a patient 34 or other individual who is resting on a support device 32, for instance, a chair, a bed, a wheel chair, a cardiac chair, a recliner, or other furniture. The double-release alarm belt 30 has a first elongated strap 36, a second elongated strap 64, and an alarm system 80. The double-release alarm belt 30 may also include a shortened strap 52. The first elongated strap 36, the second elongated strap 64, and the shortened strap 52 may be releasably affixed to one another about a first portion 112 and a second portion 114, as will be further described below. When the first elongated strap 36 and the second elongated strap 64 are disengaged about the first portion 112, the alarm system 80 may create an audible alarm. In this way, the double-release alarm belt 30 provides medical personnel with an advanced warning before the patient 34 is able to disengage the second elongated strap 64 from the shortened strap 52 about the second portion 114 to get up from the device 32.

Initially, the first elongated strap 36 will be described. The first elongated strap 36 can be seen, for instance, in FIGS. 2 and 4. The first elongated strap 36 has a first end 38, a second end 40 opposite the first end 38, and a midportion 42 located between the first end 38 and the second end 40. Additionally, the first elongated strap 36 may have an upper side 44 and an underside 46. A hook mechanism 48 may be attached to the first end 38 of the first elongated strap 36. The hook mechanism 48 may include a first ring 94 and a second ring 96. Additionally, a first fastener 50 may be associated with the first elongated strap 36. As shown, the first fastener 50 extends along the underside of the first end 38 of the first elongated strap 36. Additionally, the first elongated strap 36 may have a first handle 86 that is mounted to the upper side 44 of the first elongated strap 36 along the second end 40.

The length of the first handle 86 may be substantially the same length of the first fastener 50.

Figure 20:
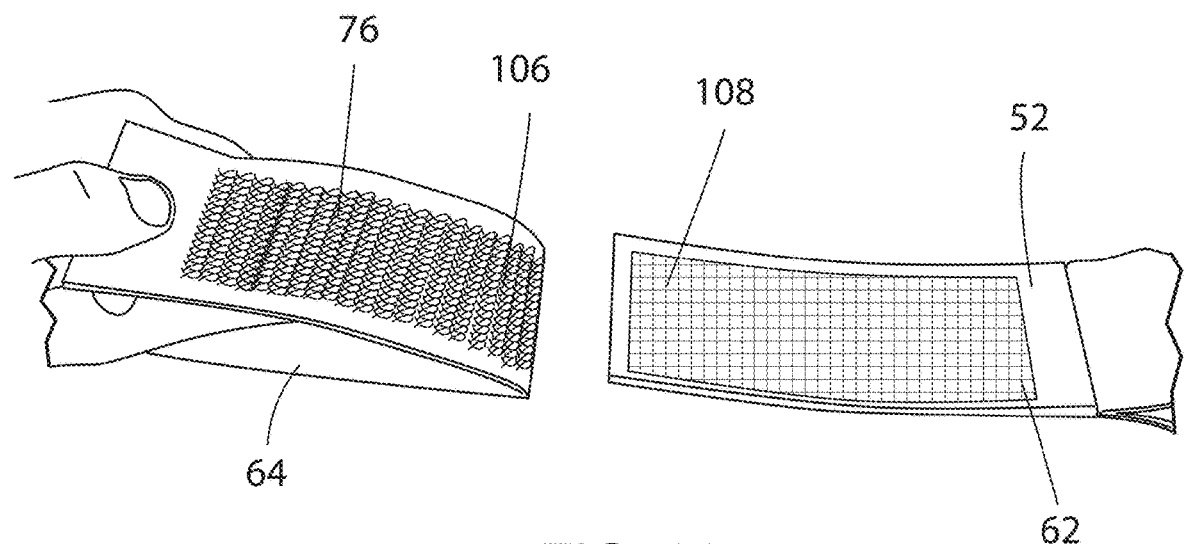
FIG. 20 illustrates another perspective view of the inventive predictive double-release alarm belt of FIGS. 5-19, where the first elongated strap is separated from the second elongated strap such that the belt is completely disengaged.

Moving on, the shortened strap 52 also has a first end 54 and a second end 56 opposite the first end 54, as well as an upper side 58 and an underside 60. The shortened strap 52 is best seen in FIG. 20. As shown, the first end 54 may be attached to the midportion 42 of the first elongated strap 36. Additionally, a second fastener 62 extends along the upper side 58 of the shortened strap 52 from the first end 54 of the shortened strap 52 to the second end 56 of the shortened strap 52.

Figure 2:
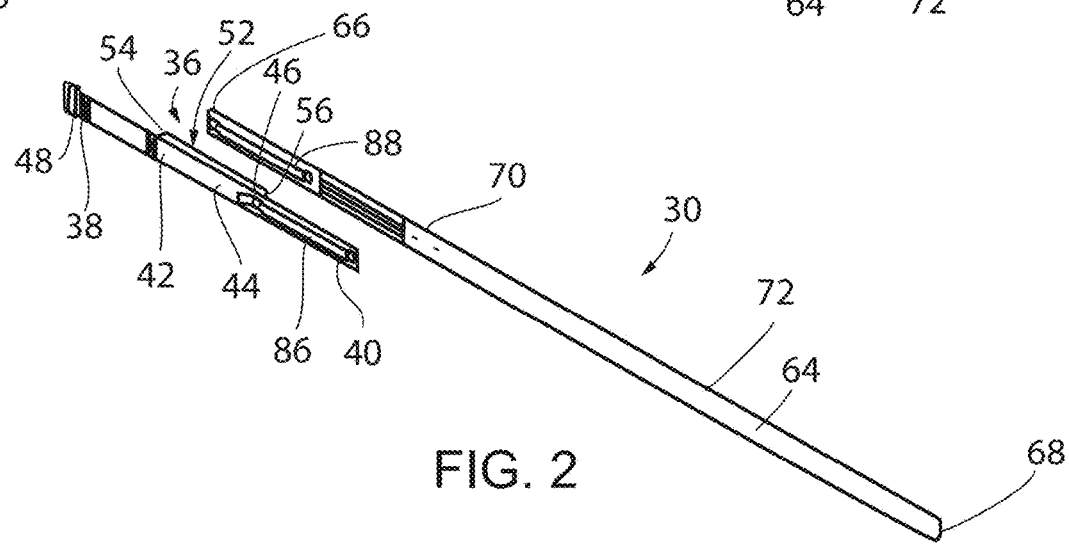
FIG. 2 illustrates an exploded perspective view of the inventive predictive double-release alarm belt of FIG. 1 where a first elongated strap associated with the belt is separate from a second elongated strap.
Figure 4:
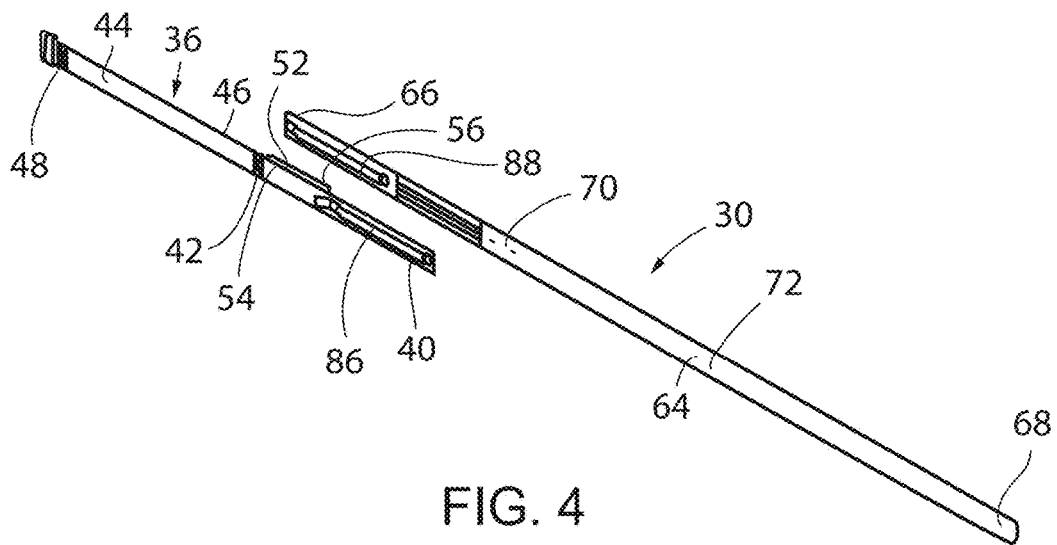
FIG. 4 illustrates an exploded perspective view of the inventive predictive double-release alarm belt of FIG. 3 where a first elongated strap associated with the belt is separate from a second elongated strap.
Figure 5:
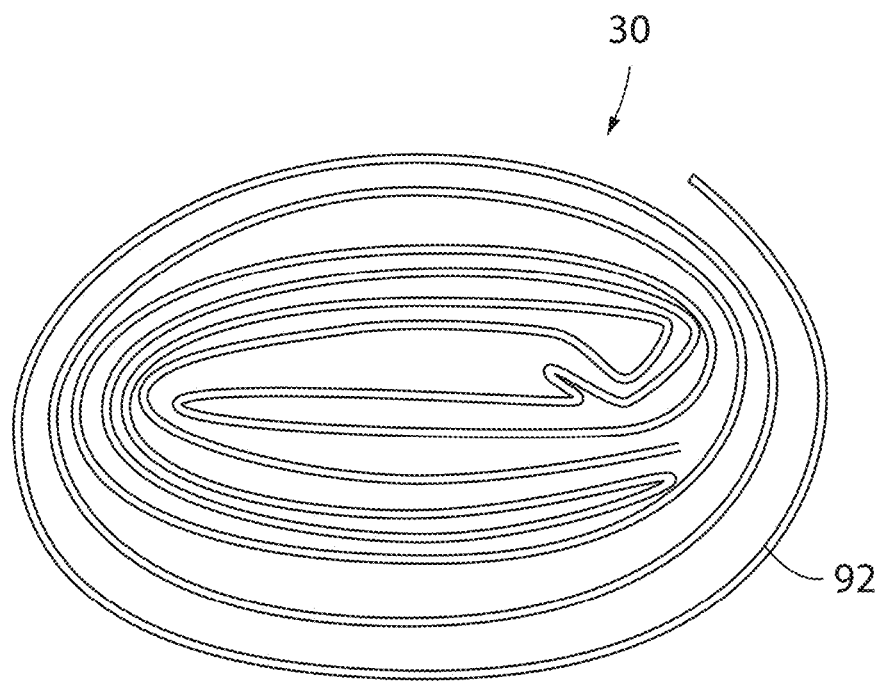
FIG. 5 illustrates a perspective view of the inventive predictive double-release alarm belt in a wrapped position.
Figure 6:
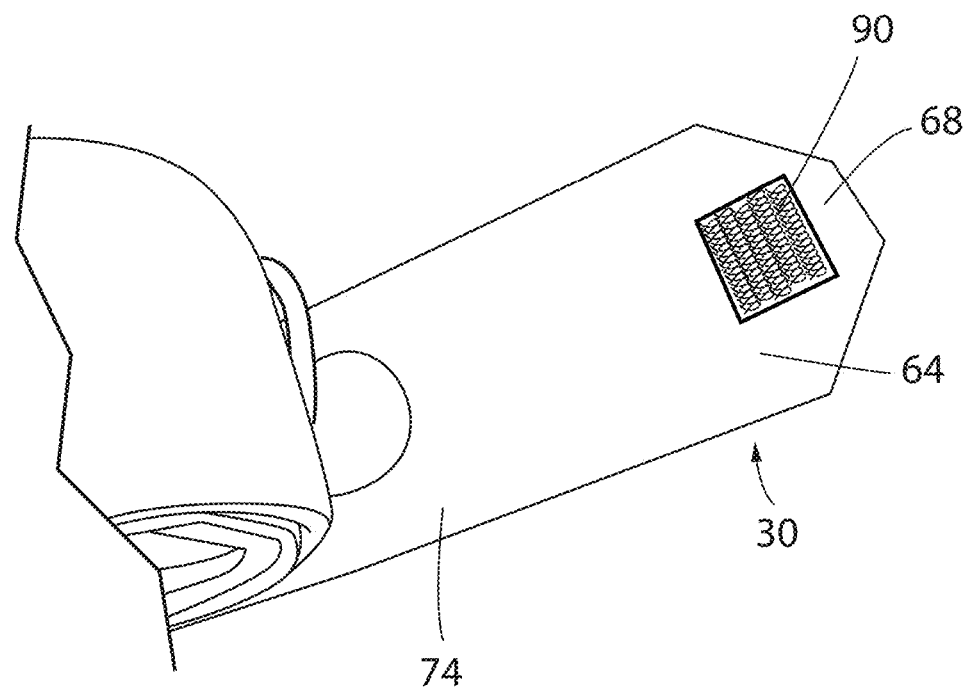
FIG. 6 illustrates a perspective view of the inventive predictive double-release alarm belt of FIG. 5 once a fifth fastener is disengaged allowing the alarm belt to be unwrapped.
Figure 7:
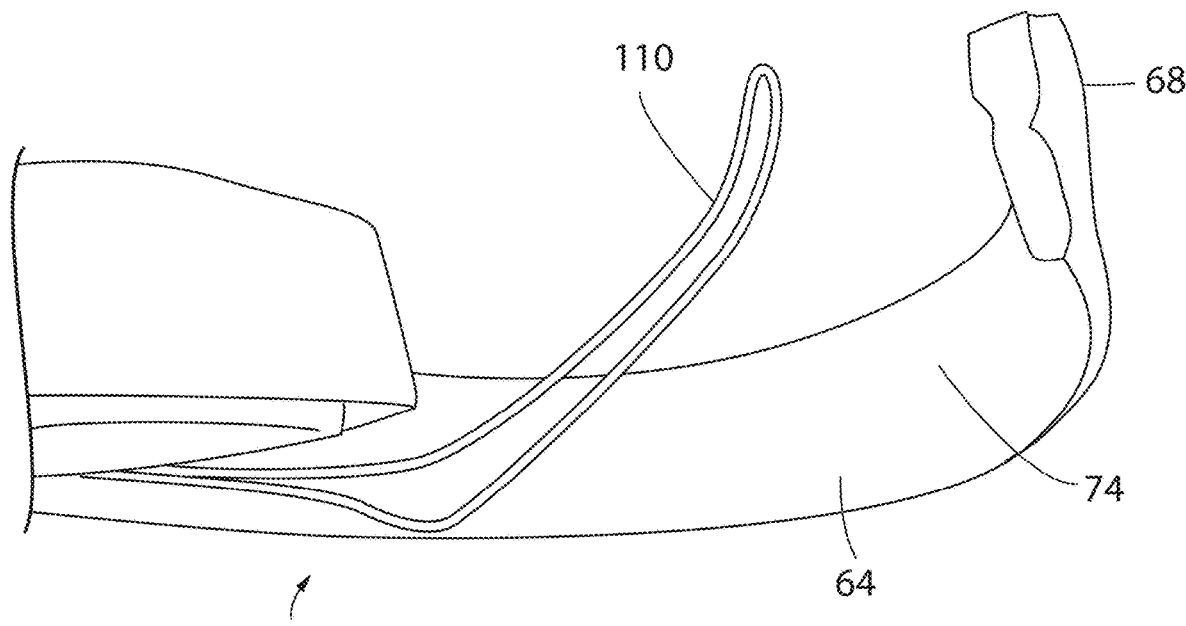
FIG. 7 illustrates a perspective view of the inventive predictive double-release alarm belt of FIGS. 5 and 6, as it is unwrapped with a cord that is associated with an alarm belt and an alarm system.
Figure 8:
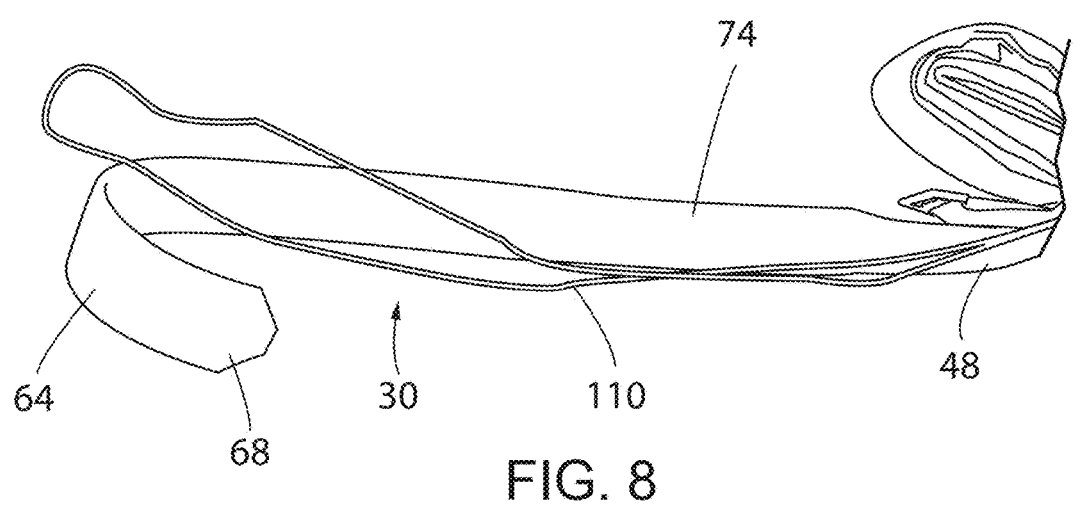
FIG. 8 illustrates a perspective view of the inventive predictive double-release alarm belt of FIGS. 5-7 in a further unwrapped position showing a second elongated strap.
Figure 9:
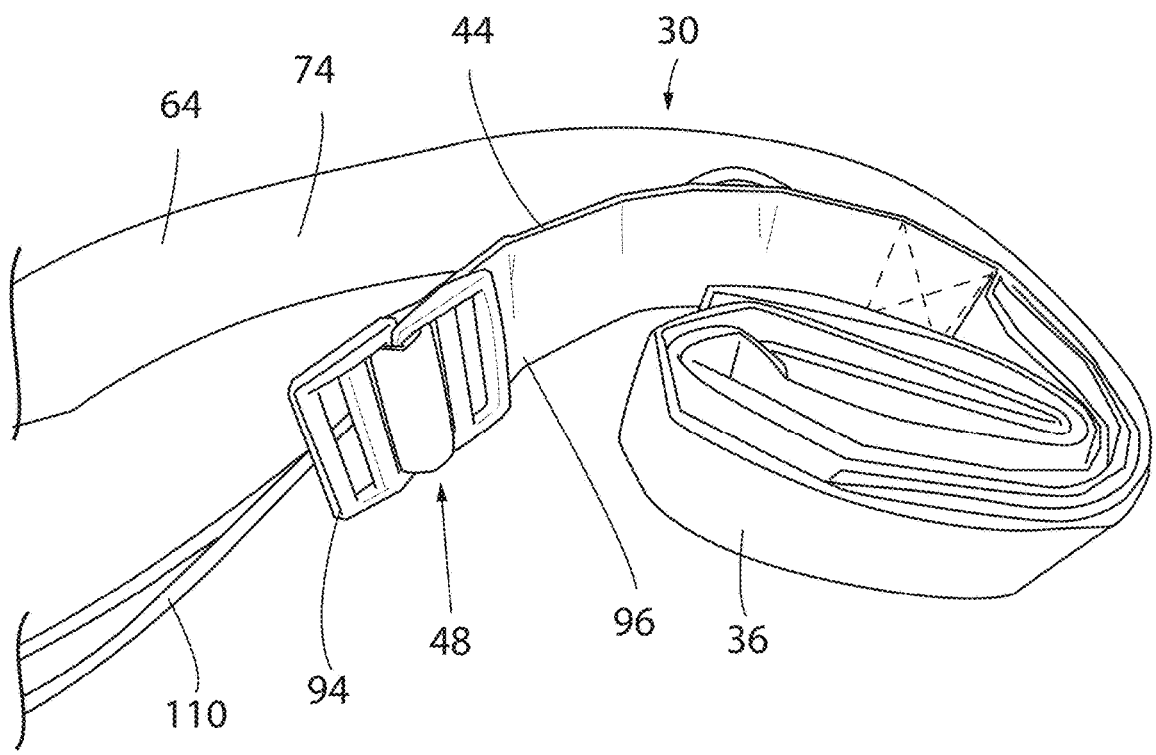
FIG. 9 illustrates a perspective view of the inventive predictive double-release alarm belt of FIGS. 5-8 in a further unwrapped position showing a first elongated strap.
Figure 10:
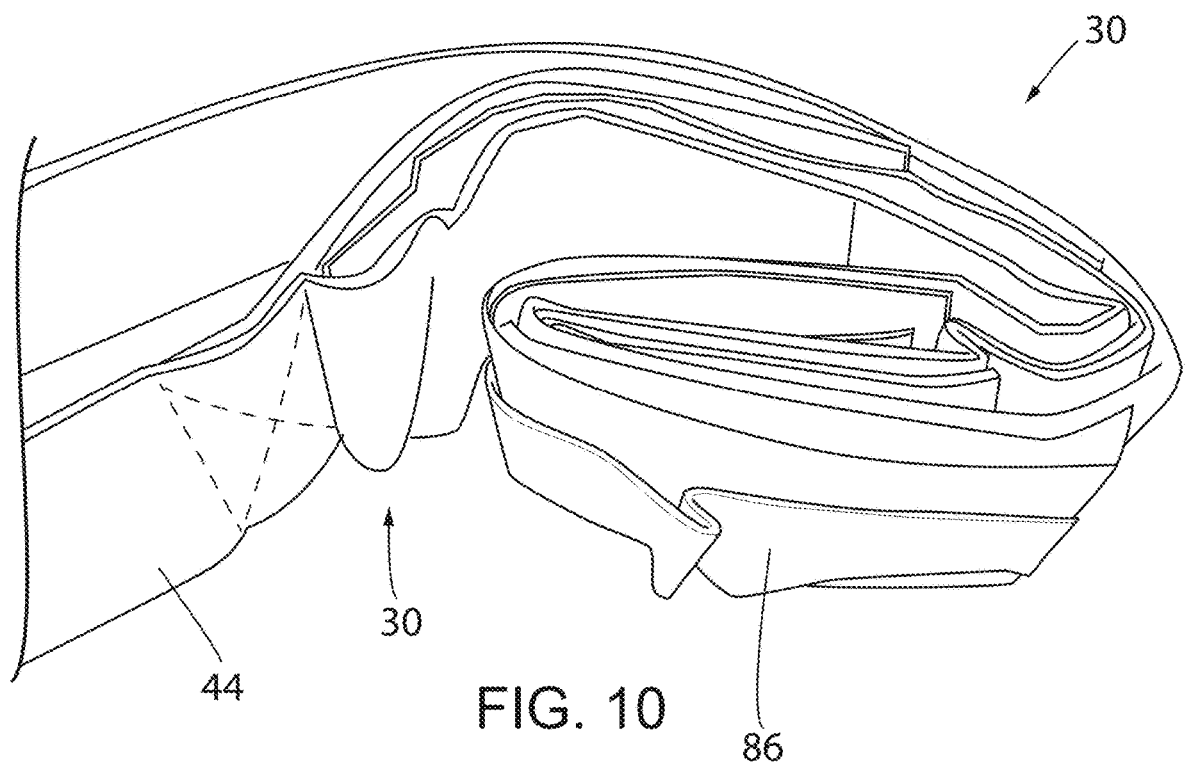
FIG. 10 illustrates a perspective view of the inventive predictive double-release alarm belt of FIGS. 5-9 in a further unwrapped position.
Figure 11:
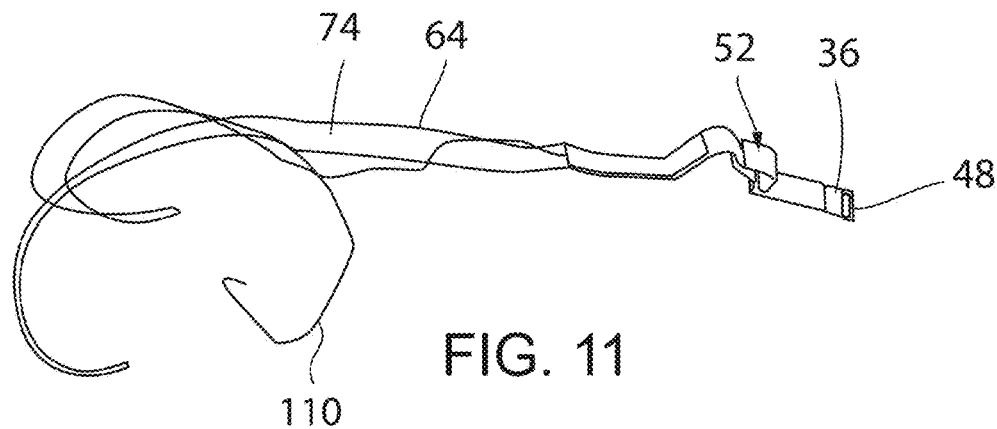
FIG. 11 illustrates a perspective view of the inventive predictive double-release alarm belt of FIGS. 5-10 in a fully unwrapped position.
Figure 12:
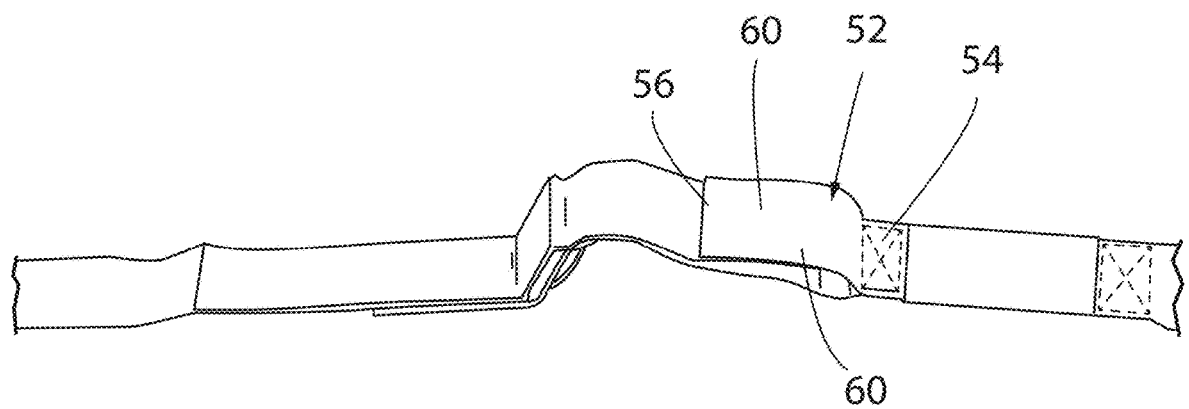
FIG. 12 illustrates another perspective view of the underside of the inventive predictive double-release alarm belt of FIGS. 5-11 in a fully unwrapped position.
Figure 13:
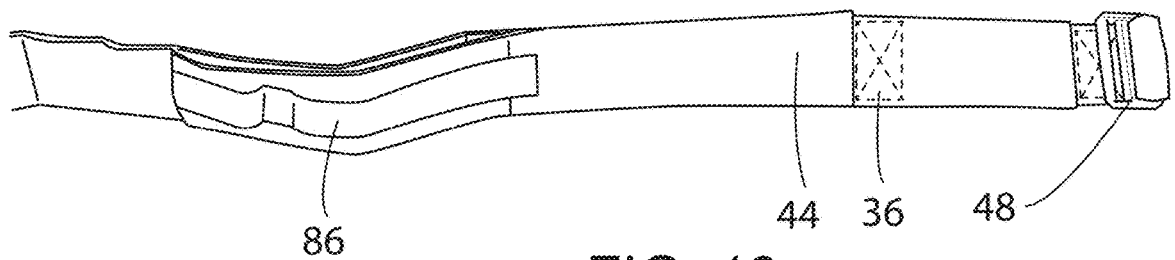
FIG. 13 illustrates another perspective view of the top side of the inventive predictive double-release alarm belt of FIGS. 5-12 in a fully unwrapped position.
Figure 14:
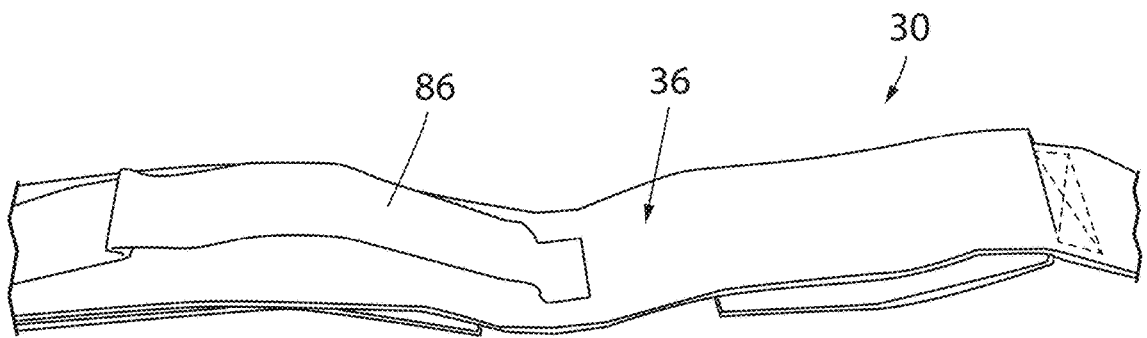
FIG. 14 illustrates another perspective view of the inventive predictive double-release alarm belt of FIGS. 5-13, and more specifically, a first handle located about a second end of the first elongated strap.

Next, the second elongated strap 64 will be described, which again is best seen in FIGS. 2 and 4. Somewhat similar to the first elongated strap 36, the second elongated strap 64 has a first end 66, a second end 68, and an intermediate portion 70 located between the first end 66 and the second end 68. The second elongated strap 64 may also have an upper side 72 and an underside 74. Additionally, a third fastener 76 and a fourth fastener 78 may be associated with the second elongated strap 64. More specifically, the third fastener 76 may be mounted along the underside 74 of the first end 66 of the second elongated strap 64. The fourth fastener 78 may be mounted along the upper side 72 of the intermediate portion 70. Also, the second elongated strap 64 may have a handle 88 that is mounted to the upper side 72 of the second elongated strap 64 along the first end 66. Further still, the second elongated strap 64 may have a fifth fastener 90 located about the second end 68. The fifth fastener 90 can hold the double-release alarm belt 30 in a wrapped position 92, as shown in FIG. 5. FIGS. 6-11 show the double-release alarm belt 30 as it is unwrapped. Additionally, the fifth fastener 90 can be used to secure the second end to the double-release alarm belt 30 once installed about the patient 34 and the device 32.

As shown in FIGS. 6, 15, 16, 17, 19, and 20, each of the fasteners 50, 62, 76, 78 may be selected from one of a hook fastener 106 and a loop fastener 108. Other types of fasteners could similarly be used, such as snaps, adhesive, ties, and the like. Additionally, as shown, the compatible fasteners can be color-coded to simplify the assembly or re-assembly process. For instance, the first fastener 50 and the fourth fastener 78 are made of white hook and loop fasteners. Similarly, the second fastener 62 and the third fastener 76 are made of blue hook and loop fasteners. In this way, medical personnel can easily re-assemble the double-release alarm belt 30 without risk of engaging the wrong fasteners with one another. This is especially helpful where the double-release alarm belt 30 is reusable. Also, the handles 86, 88 can be a different color from the rest of the double-release alarm belt 30, so that they can more easily be seen and distinguished from the other parts of the belt 30. For instance, the handles 86, 88 may be a fluorescent yellow.

Each of the first elongated strap 36, the shortened strap 52, and the second elongated strap 64 may be disposable. Additionally, the cord 110, which can be disengaged from the alarm system 80, can also be disposable. For instance, the disposable version of the belt 30 could be made of a silver conductive fabric, as well as a nylon or foam laminate. These materials are typically less expensive in comparison to the materials needed to manufacture previous reusable belts. Additionally, the disposable version could have hook and loop fasteners as opposed to buckles, which can be expensive. For instance, the disposable materials may be 25-75% less expensive than those associate with traditional belts, and more preferably 40-50% less expensive than traditional belts. Such a configuration would be especially appealing in situations where the double-release alarm belt 30 is used in hospital settings or other environments where sterility must be maintained. By having an affordable disposable alarm belt 30, the belt 30 can simply be thrown away after use without the need to sterilize a previously-used belt, which can be time-consuming and costly. Alternatively, in situations where sterility is not a concern, the double-release alarm belt 30 could be reusable. For instance, such a configuration could include materials, such as nylon webbing, seat belt buckles, biothan webbing, and silver conductive fabric. Alternatively, any aspect of the belt 30 could be made of any other number of materials, including non-woven materials, such as plastic or paper. Regardless of the material, the belt 30 is preferably configured to be able to withhold forces of over 100 pounds before failure.

Possible dimensions of the first elongated strap 36, the shortened strap 52, and the second elongated strap 64 will now be described. However, it should be noted that straps of various dimensions may be used to accommodate different uses. Additionally, it should be noted that larger straps could be used for patients with larger waist sizes or for use with larger chairs, beds, cardiac chairs, recliners, and the like.

For instance, the length of the double-release alarm belt 30 could be approximately 60-100 inches in length and, more preferably, approximately 78 inches, as shown in FIGS. 1 and 2. Additionally, typical belts 30 will be approximately 2 inches in height, although again, different dimensioned belts could be used as required by the specific use. In such an embodiment, the first elongated strap 36 could be 20-40 inches, and more preferably 27.5 inches. Additionally, in this embodiment the second elongated strap 64 could be between 75-105 inches, and more preferably 90 inches.

Figure 3:
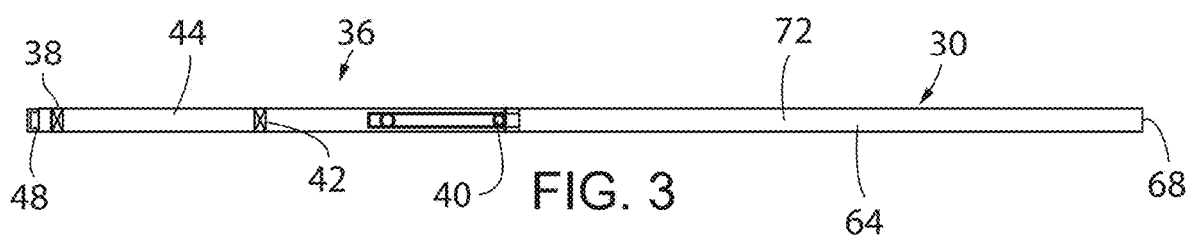
FIG. 3 illustrates a side elevation view of another inventive predictive double-release alarm belt of the present invention.

An alternative double-release alarm belt 30 could be much longer, for instance, the length of the double-release alarm belt could be approximately 70-110 inches in length and, more preferably, approximately 92 inches as shown in FIGS. 3 and 4. Additionally, typical belts 30 will be approximately 2 inches in height, although again, different dimensioned belts could be used as required by the specific use. In this embodiment, the first elongated strap 36 could be 25-55 inches, and more preferably 40 inches. Additionally, in this embodiment the second elongated strap 64 could be between 75-105 inches, and more preferably 90 inches. As such, the same second elongated strap 64 could be used with either embodiment, with different first elongated straps 36 being used, depending on how the belt 30 will be used.

Functionality of the cord 110 and alarm system 80 will now be described. The cord 110 is embedded within the second elongated strap 64 and monitors the locations of the first fastener 50 and fourth fastener 78. More specifically, when the fourth fastener 78 is pulled away from the first fastener 50, the cord 110 transmits this information to the alarm system 80, and the alarm system 80 generates an audible alarm. For instance, an electrical circuit can be completed where the first and fourth fasteners 50, 78 are connected to one another. When these fasteners 50, 78 are pulled apart from one another, the electrical circuit can be interrupted. Once the circuit is interrupted, the alarm can be triggered. Alternatively, a cord need not be included with the system, but instead, a wireless or Bluetooth system could be used to wirelessly trigger the alarm system 80 to generate the audible alarm when the first fastener 50 and the fourth fastener 78 are separated. The double-release alarm belt 30 can be used with any number of various fall-prevention alarm systems, as known to those of skill in the art. For instance, the belt 30 can be used with various POSEY fall alarms, including POSEY KEEPSAFE, POSEY KEEP- SAFE DELUXE, POSEY KEEPSAFE SCOUT, and POSEY SITTER ELITE fall alarms.

Figure 21:
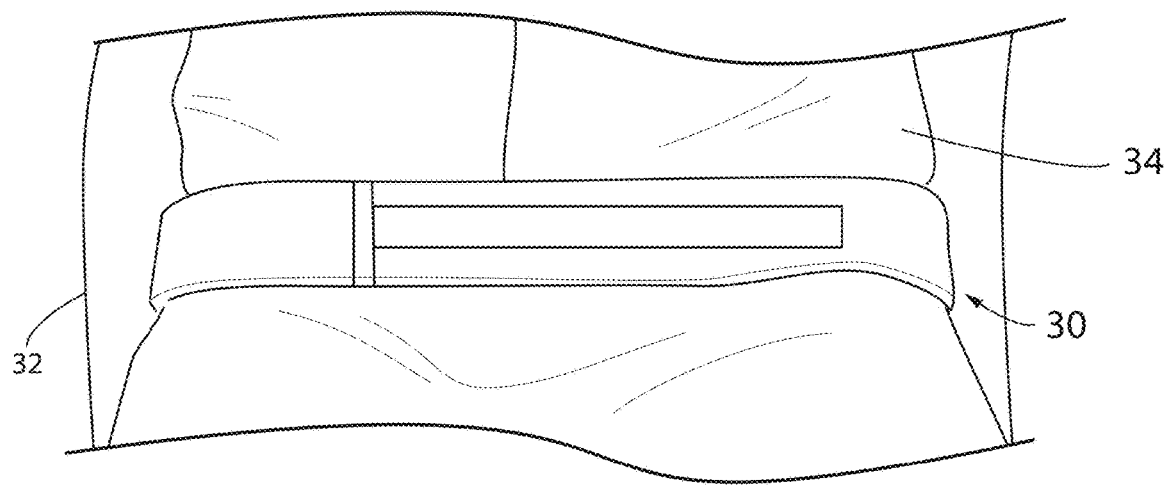
Figure 22:
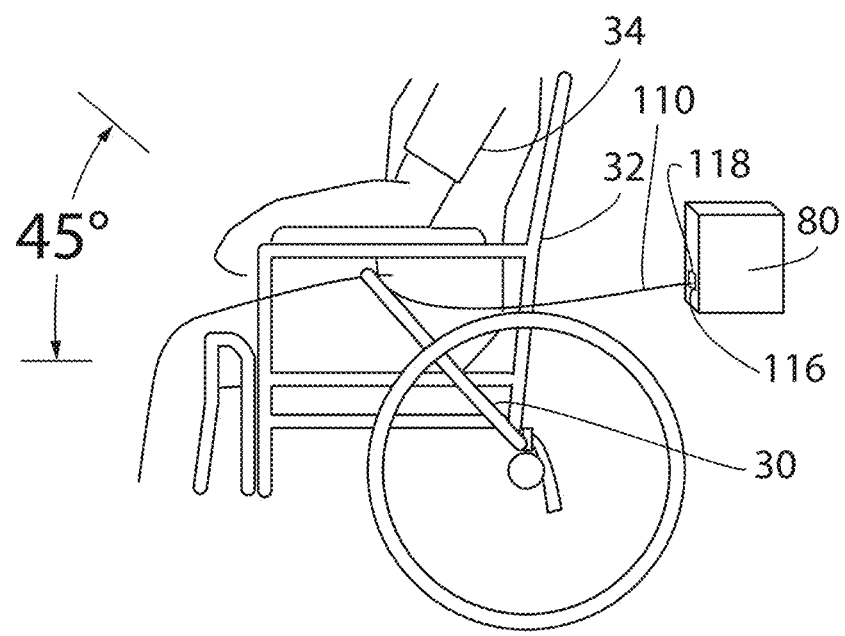
Figure 23:
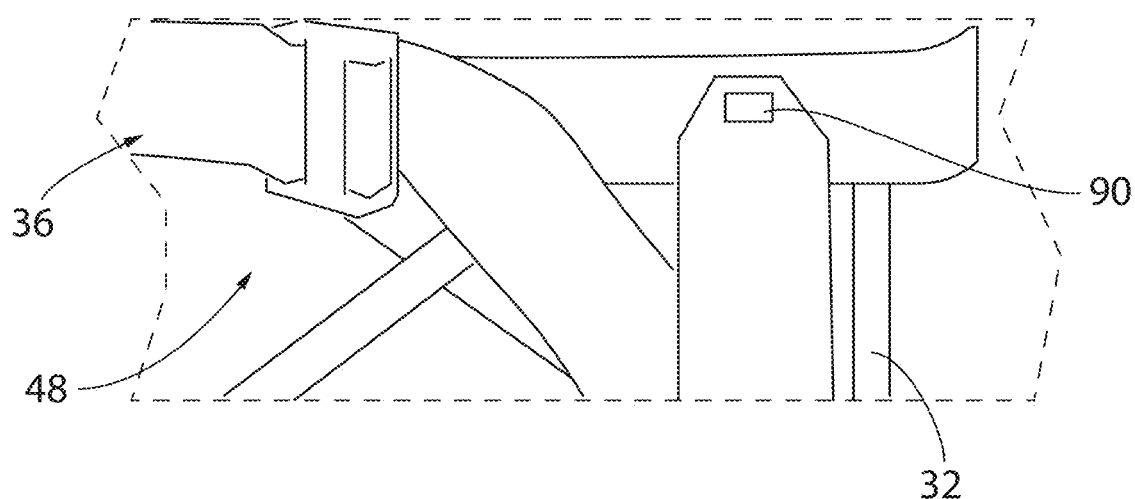
FIG. 23 illustrates a perspective view of a hook mechanism associated with the first elongated strap where the fifth fastener is engaged with the belt so that the excess strap at the second end of the second elongated strap is secured.
Figure 24:
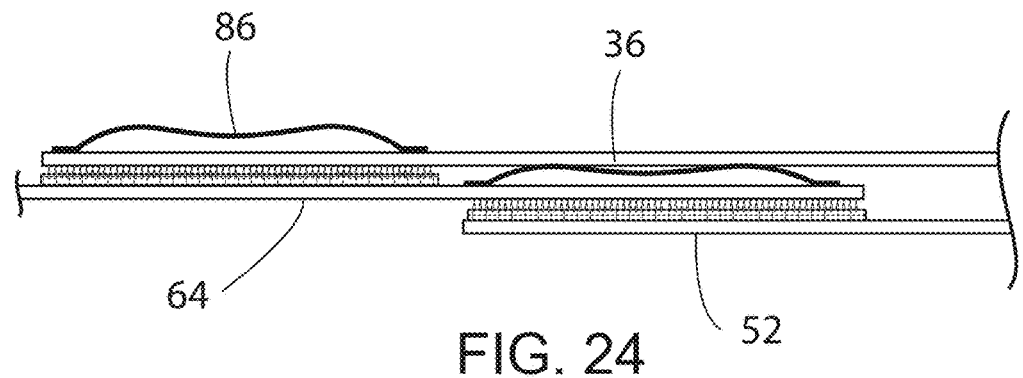
FIG. 24 illustrates a simplified side elevation view of the inventive predictive double-release alarm belt where the first elongated strap, the shortened strap, and the second elongated strap are attached to one another.

To assemble the double-release alarm belt 30, the first fastener 50 is releasably engaged with the fourth fastener 78 and the second fastener 62 is releasably engaged with the third fastener 76. Once the double-release alarm belt 30 has been assembled, it can be installed about the patient 34. Initially the patient 34 is seated or laid onto a piece supporting equipment device 32, for instance, chairs, beds, recliners, and the like, as shown in FIG. 21. The belt 30 is wrapped around the patient's waist with the hook mechanism 48 located behind the patient 34. See FIGS. 21 and 22. Preferably, the belt 30 is located at approximately a 45-degree angle relative to the ground, although the specific angle could vary depending on the comfort of the patient 34, as shown in FIG. 22. The position of the first end 38 of the first elongated strap 36 and the second end 68 of the second elongated strap 64 should be positioned behind the device 32, as shown a chair back, as low as possible so that the belt 30 cannot slide up off the chair. Next, the second end 68 of the second elongated strap 64 is threaded through the hook mechanism 48, as shown in FIG. 23. More specifically, the second end 68 of the second elongated strap 64 is first threaded through the first ring 94 and the second ring 96, then back over one ring and through the other, as known to one of ordinary skill in the art. The second end 68 is then tightened so that it is securely held within the hook mechanism 48 so that the belt 30 is snug about the patient 34 and the supporting device 32. The medical personnel can verify that the belt 30 is not overly constricting by sliding an open hand between the belt 30 and the patient 34. Finally, a fifth fastener 90 located on the second end 68 of the second elongated strap 64 is engaged with a side of the double belt 30 as shown in FIG. 23. In this way, the loose second end 68 does not hang down on to the floor. Finally, the alarm cord 110 is connected to the alarm system 80 by inserting a jack 116 into a port 118 of the alarm system. Thereafter, the alarm system 80 is turned on.

Figure 15:
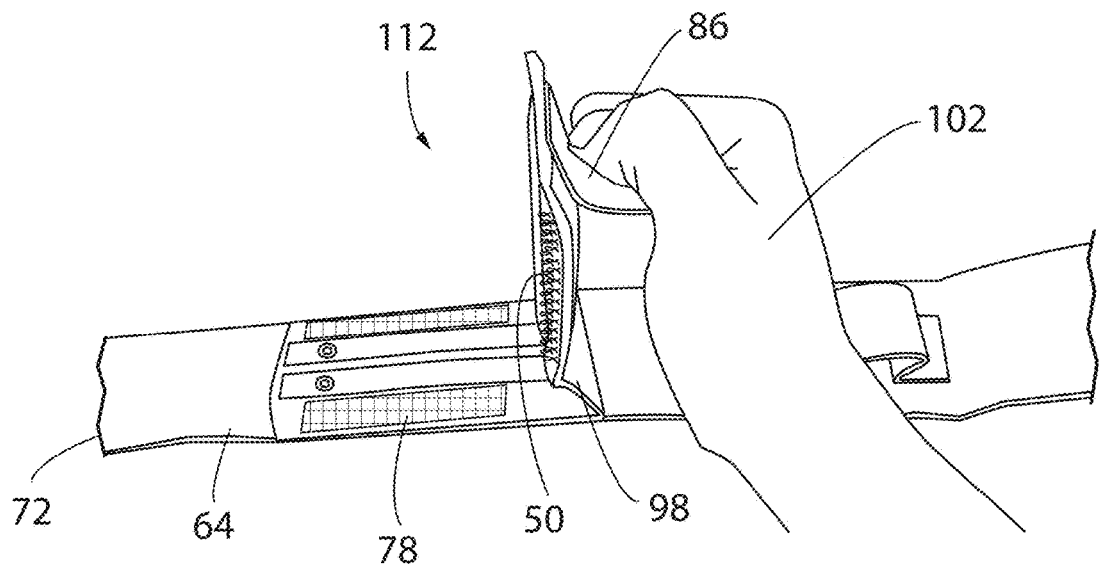
FIG. 15 illustrates another perspective view of the inventive predictive double-release alarm belt of FIGS. 5-14 and, more specifically, the second end of the first elongated strap being pulled in a first direction away from an intermediate portion of the second elongated strap to separate a first fastener from a fourth fastener.
Figure 16:
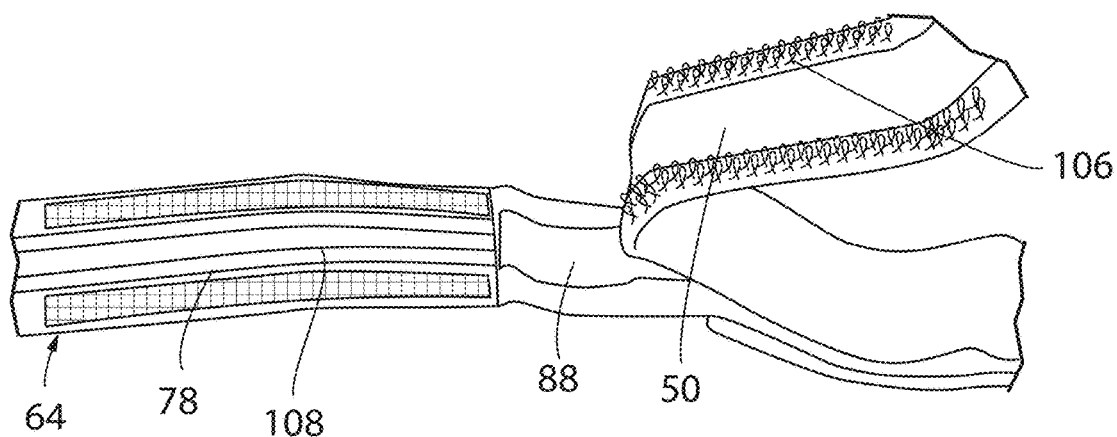
FIG. 16 illustrates another perspective view of the inventive predictive double-release alarm belt of FIGS. 5-15 and, more specifically, the second end of the first elongated strap being pulled away from an intermediate portion of the second elongated strap after the bond between the first fastener and the fourth fastener has been broken.
Figure 17:
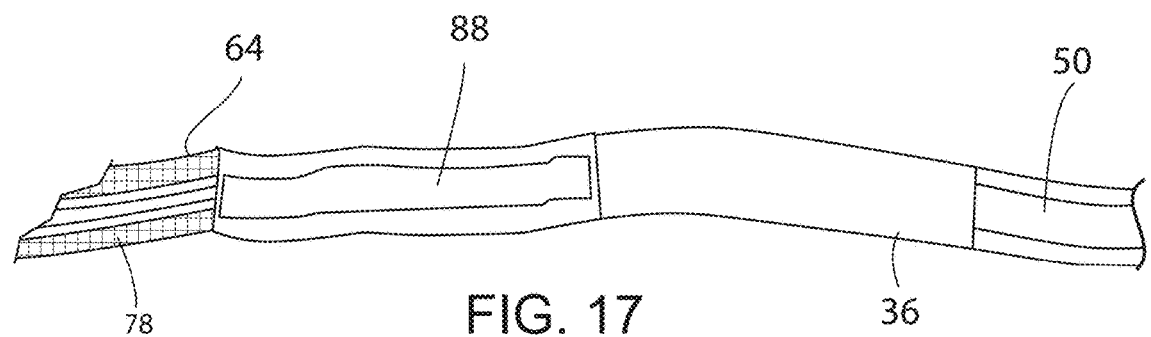
FIG. 17 illustrates another perspective view of the inventive predictive double-release alarm belt of FIGS. 5-16 and, more specifically, a second handle mounted to an upper surface of the first end of the second elongated strap once the bond between the first fastener and the fourth fastener has been broken.
Figure 18:
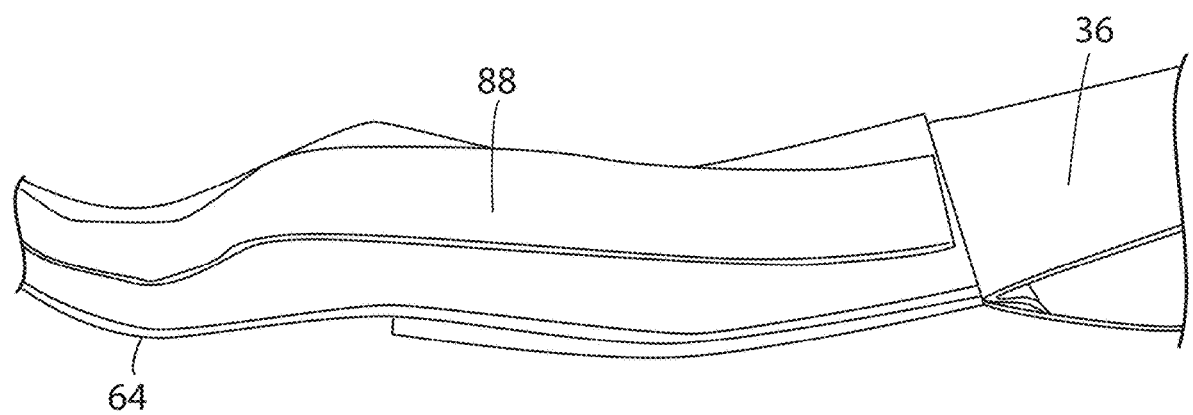
FIG. 18 illustrates another perspective view of the inventive predictive double-release alarm belt of FIGS. 5-17 and, more specifically, a detailed view of the second handle mounted to an upper surface of the first end of the second elongated strap.
Figure 19:
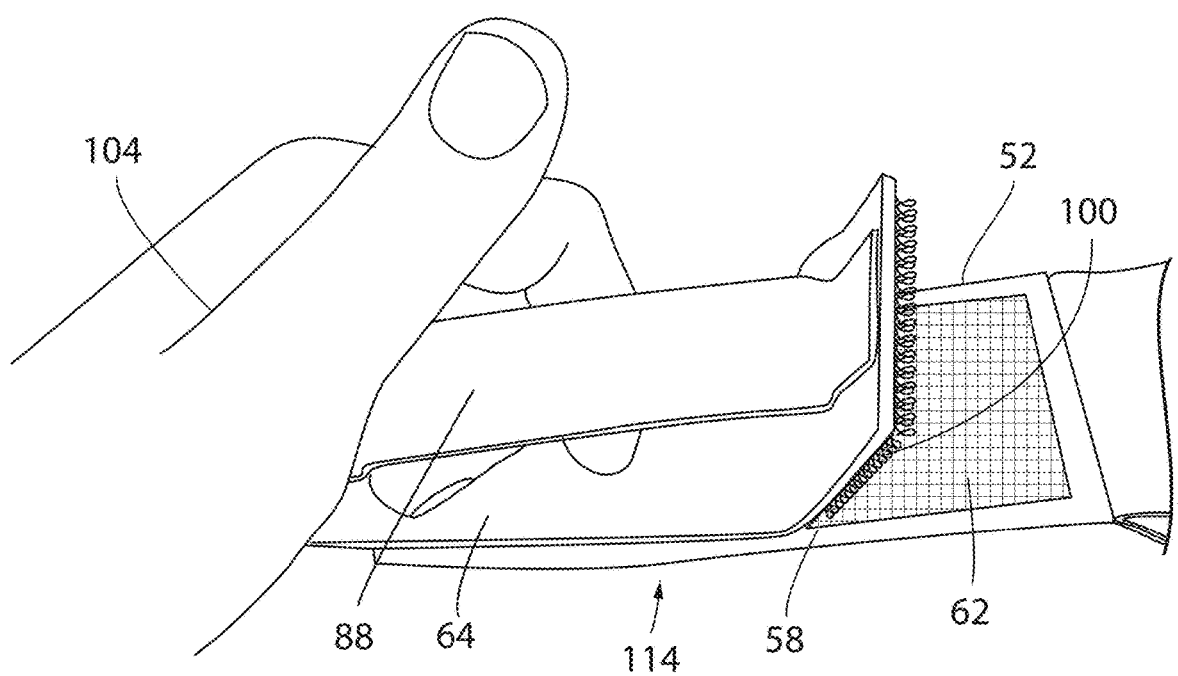
FIG. 19 illustrates another perspective view of the inventive predictive double-release alarm belt of FIGS. 5-18 and, more specifically, a first end of the second elongated strap being pulled in a second direction away from an upper side of a shortened strap attached to the first elongated strap to separate a second fastener from a third fastener.
Figure 25:
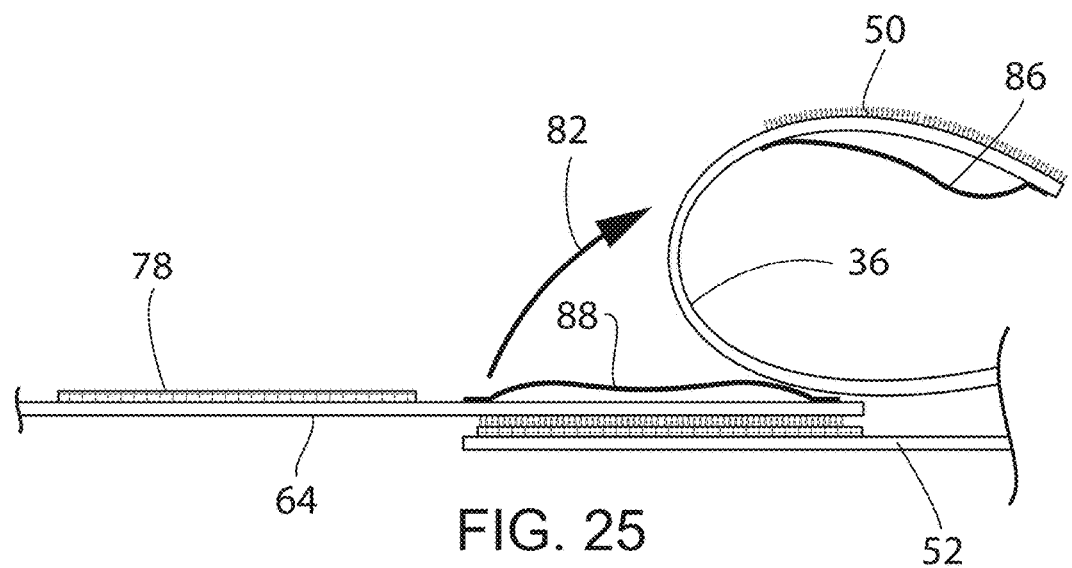
FIG. 25 illustrates a simplified side elevation view of the inventive predictive double-release alarm belt where the first elongated strap is being pulled in a first direction away from the intermediate portion of the second elongated strap to separate the first fastener from the fourth fastener.
Figure 26:
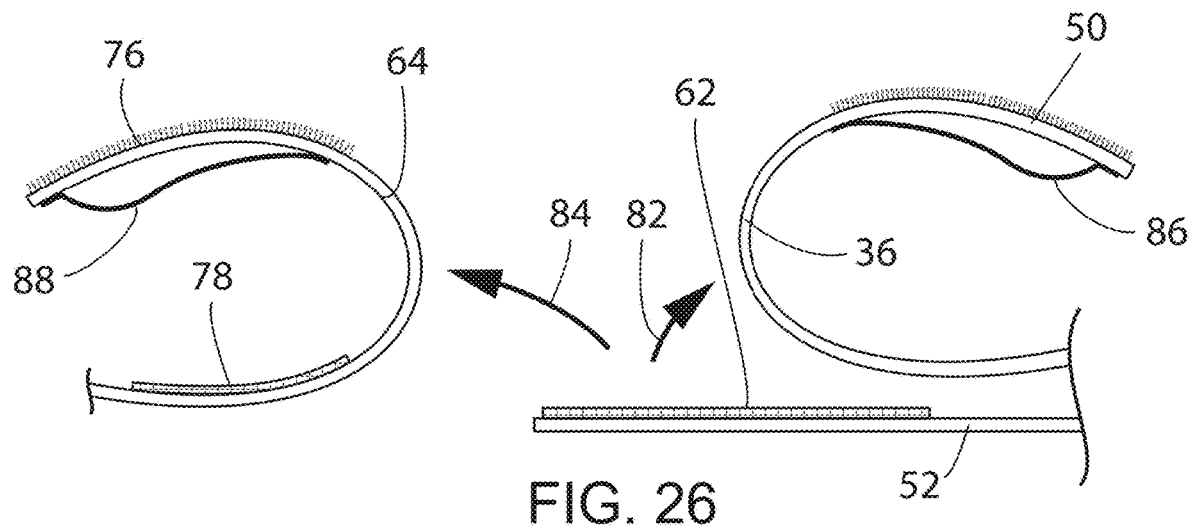
FIG. 26 illustrates a simplified side elevation view of the inventive predictive double-release alarm belt where the second elongated strap is being pulled in a second direction opposite the first direction from the shortened strap that is attached to the first elongated strap to separate the second fastener from the third fastener.

Once the belt 30 has been installed, the position of the patient 34 about the device 32 can be monitored. In the event the patient 34 begins to disengage the double-release alarm belt 30, the medical personnel will be notified. This first occurs when the first fastener 50 and fourth fastener 78 are pulled apart with a first force 102, such that the bond 98 between these fasteners 50, 78 is interrupted, as seen in FIGS. 15, 16, and 25. Preferably, due to the locations of the fasteners 50, 78 relative to the first elongated strap 36 and the second elongated strap 64, the separation of the first fastener 50 and the fourth fastener 78 occurs by pulling the second end 56 of the first elongated strap 36 in a first direction 82. See FIG. 25. As described above, once the first fastener 50 and the fourth fastener 78 are pulled apart, the alarm will sound to notify medical personnel that the patient 34 is trying to get out of the device 32. Next, the second fastener 62 and the third fastener 76 are pulled apart with a second force 104, such that the bond 100 between these fasteners 62, 76 is interrupted as seen in FIGS. 19, 20, and 26. The first force 102 required to disengage the first fastener 50 and the fourth fasteners 78 is less than the second force 104 required to disengage the second fastener 62 and the third fastener 76. Due to the locations of the fasteners 62, 76 relative to the first elongated strap 36 and the second elongated strap 64, the separation of the second fastener 62 and the third fastener 76 occurs by pulling the first end 66 of the second elongated strap 64 in a second direction 84. See FIG. 26. Preferably, the first direction 82 is in the opposite direction as the second direction 84. This results in increased time and difficulty for the patient 34 to remove the double-release alarm belt 30 than if the patient 34 simply had to repeatedly pull two separate belts in the same direction.

Furthermore, the bond 98 between the first fastener 50 and the fourth fastener 78 can be weaker than the bond 100 between the second fastener 62 and the third fastener 76. In this way, the patient 34 can more easily disengage the first fastener 50 from the fourth fastener 78, at which time the alarm will be sounded. Thereafter, due to the stronger bond 100 between the second fastener 62 and the third fastener 76, it will be more difficult for the patient 34 to disengage these fasteners 62, 76. This makes it more difficult for the second bond 100 to be broken, which increases the amount of time that medical staff has to approach the patient 34 after the initial alarm has been sounded. In this way, potential falls of the patient can be minimized.

A method of using the double-release alarm belt 30 will now be described. Initially, the double-release alarm belt 30 is wrapped around the patient 34 as well as the device 32. Next, the first end 38 is engaged with the second end 68 to secure the ends 38, 68 to one another. Additionally, an alarm system 80 is connected to the double-release alarm belt 30, for instance, by a cord 110. Next, the first elongated strap 36 can be disengaged from the second elongated strap 64 about a first portion 112. This can occur when the first handle 86 is pulled to disengage the first elongated strap 36 from the second elongated strap 64 about the first portion 112. Once the straps 36, 64 are disengaged about the first portion 112, the alarm system 80 creates an audible alarm. For instance, this may occur where an electrical circuit is interrupted. Alternatively, various sensors can be used to detect when the straps 36, 64 are disengaged about the first portion 112. Of course, the alarm may be sounded using any other ways known to those of ordinary skill in the art to detect when the two straps 36, 64 are disengaged from one another. Thereafter, the first elongated strap 36 can be disengaged from the second elongated strap 64 about a second portion 114. This can occur when the second handle 88 is pulled to disengage the first elongated strap 36 from the second elongated strap 64 about the second portion 114. Thereafter, the patient 34 is released such that he or she can move away from the device 32. Additional steps may include threading the second end 68 of the double-release alarm belt 30 through the first ring 94 and the second ring 96 associated with the first end 38 of the belt 30 until the double-release alarm belt 30 is snug about the patient 34. Also, the second end 68 of the double-release alarm belt 30 may be held in place using a hook and loop fastener 90.

Figure 27:
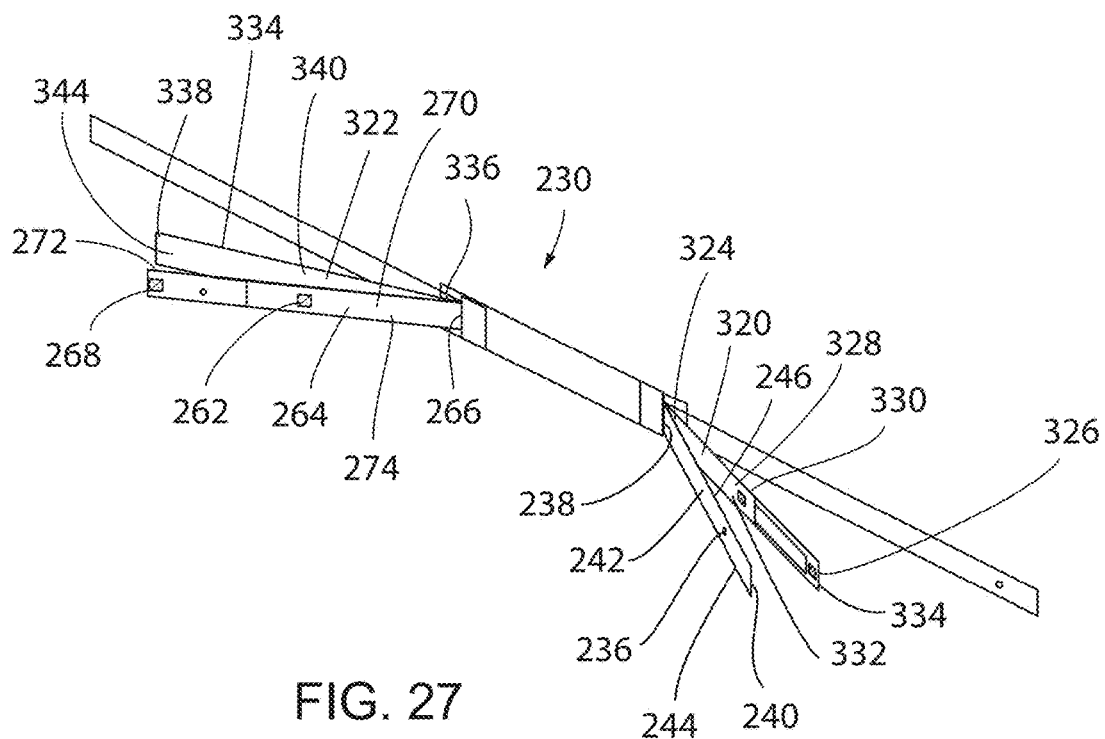
FIG. 27 illustrates an isometric view of another embodiment of the inventive predictive alarm belt of the present invention.
Figure 28:
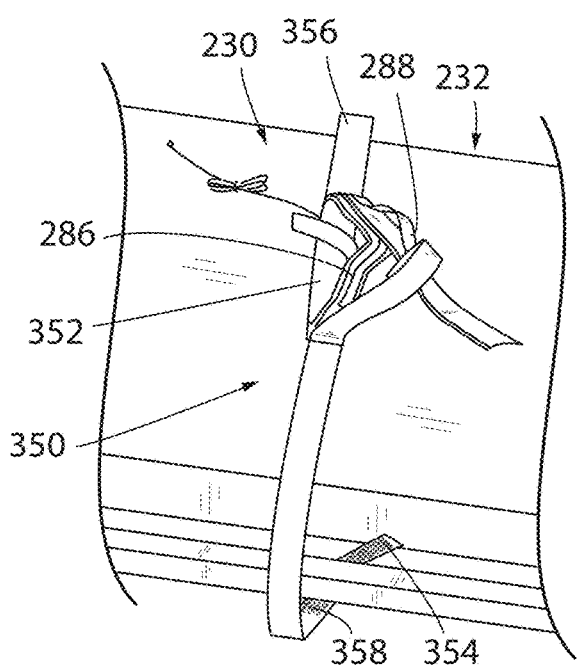
FIG. 28 illustrates a perspective view of the inventive predictive alarm belt of FIG. 27, as it is being secured to a device or piece of furniture.
Figure 29:
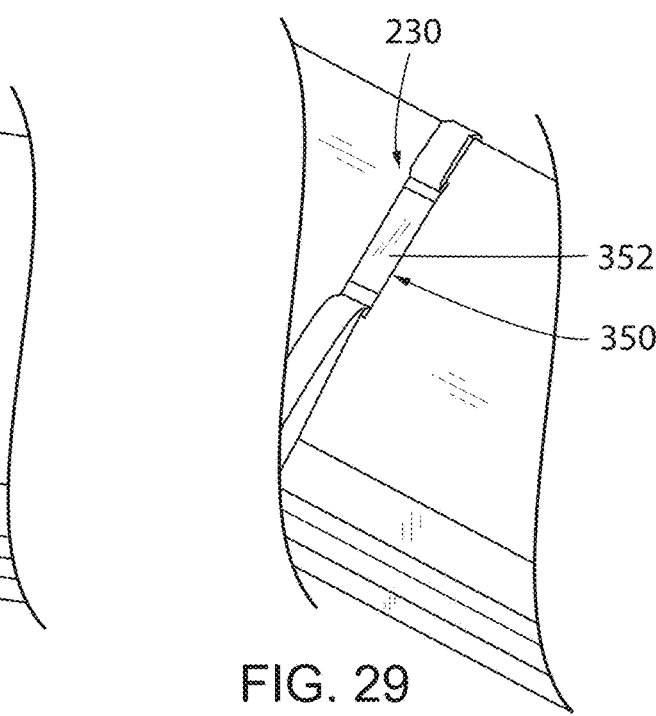
FIG. 29 illustrates a perspective view of the inventive predictive alarm belt before the elongated straps are engaged with one another.

Another embodiment of the double-release alarm belt 230 is shown in FIGS. 27-34. The components found in FIGS. 27-34 that have been previously described will be designated by the same reference numbers as those provided above incremented by 200. The double-release alarm belt 230 is used to monitor the position of a patient 234 or other individual who is resting on a support device 232, as shown a bed. The double-release alarm belt 230 has a first elongated strap 236, a second elongated strap 264, and an alarm system 280. The double-release alarm belt 230 may also include a third elongated strap 320 and a fourth elongated strap 322. Additionally, the double-release alarm belt 230 includes a base 350 with a middle portion 352 and first and second ends 354, 356 having fasteners that can wrap around the support device 232. For instance, the ends 354, 356 could have hook-and-loop fasteners 358, as seen in FIG. 28. Of course, other fasteners could similarly be used to secure the belt 230 to the device 232. Once the ends 354, 356 are wrapped around the device 232, as shown frame portions of the bed, they can be fastened to themselves to secure the belt 230 in place. The middle portion 352 may be made of a thin, low-friction material that allows the patient 234 to lay on the middle portion 352 without feeling the middle portion 352. Additionally, the middle portion 352 can be made of a durable, thin, moisture-wicking fabric that ensures comfort of the patient 234 once the belt 230 is installed. This ensures that integrity about the belt 230 can be maintained while the patient 234 does not feel the middle portion 352.

The first elongated strap 236 and the second elongated strap 264 may be releasably affixed to one another about a first portion 312, and the third elongated strap 320 and the fourth elongated strap 322 may be releasably affixed to one another about a second portion 314, as will be further described below. When the first elongated strap 236 and the second elongated strap 264 are disengaged about the first portion 312, the alarm system 80 may create an audible alarm. In this way, the double-release alarm belt 230 provides medical personnel with an advanced warning before the patient 234 is able to disengage the third elongated strap 320 from the fourth elongated strap 322 about the second portion 314 to get up from the device 232.

Initially, the first elongated strap 236 will be described. The first elongated strap 236 can be seen, for instance, in FIG. 27. The first elongated strap 236 has a first end 238, a second end 240 opposite the first end 238, and a midportion 242 located between the first end 238 and the second end 240. Additionally, the first elongated strap 236 may have an upper side 244 and an underside 246. Also, a first fastener 250 may be associated with the first elongated strap 236. As shown, the first fastener 250 extends along the upper side 244 of the first elongated strap 236.

Still looking to FIG. 27, the second elongated strap 264 will be described. The second elongated strap 264 has a first end 266, a second end 268 opposite the first end 266, and a midportion 270 located between the first end 238 and the second end 240. Additionally, the second elongated strap 264 may have an upper side 272 and an underside 274. Further, a second fastener 262 may be associated with the second elongated strap 264. As shown, the second fastener 262 extends along the underside 274 of the second elongated strap 264. Additionally, the second elongated strap 264 may have a first handle 286 that is mounted to the upper side 272 of the second elongated strap 264.

Moving on, the third elongated strap 320 will be described. The third elongated strap 320 has a first end 324, a second end 326 opposite the first end 324, and a midportion 328 located between the first end 324 and the second end 326. Additionally, the third elongated strap 320 may have an upper side 330 and an underside 332. Further, a third fastener 334 may be associated with the third elongated strap 320. As shown, the third fastener 334 extends along the underside 332 of the third elongated strap 320. Further still, the third elongated strap 320 may have a second handle 288 that is mounted to the upper side 330 of the third elongated strap 320.

Moving on, the fourth elongated strap 322 will be described. The fourth elongated strap 322 has a first end 336, a second end 338 opposite the first end 336, and a midportion 340 located between the first end 336 and the second end 338. Additionally, the fourth elongated strap 322 may have an upper side 342 and an underside 344. Also, a fourth fastener 346 may be associated with the fourth elongated strap 322. As shown, the fourth fastener 346 extends along the upper side 342 of the fourth elongated strap 322.

Figure 30:
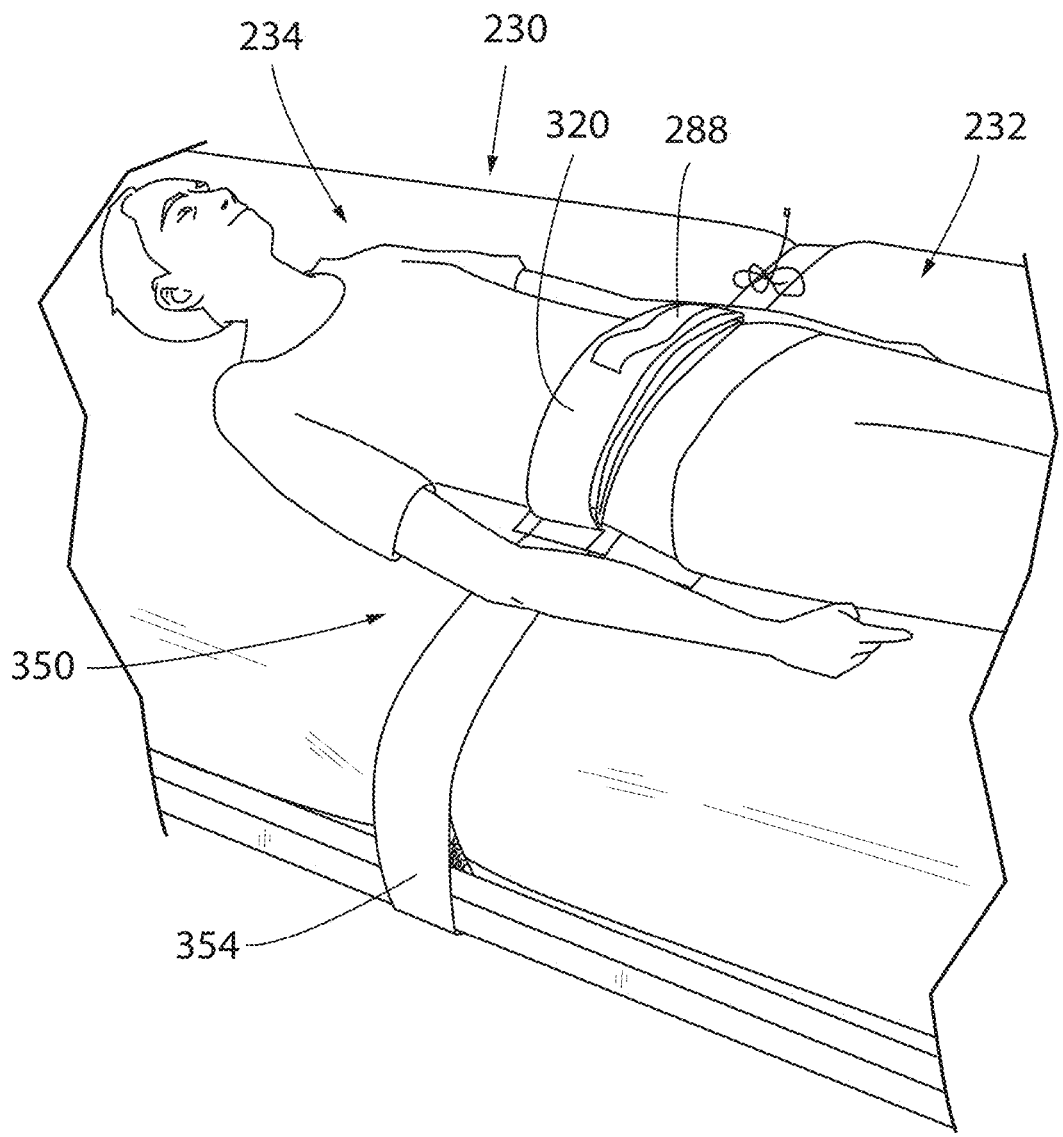
FIG. 30 illustrates a perspective view of the inventive predictive alarm belt after a patient is secured to the device or piece of furniture.
Figure 31:
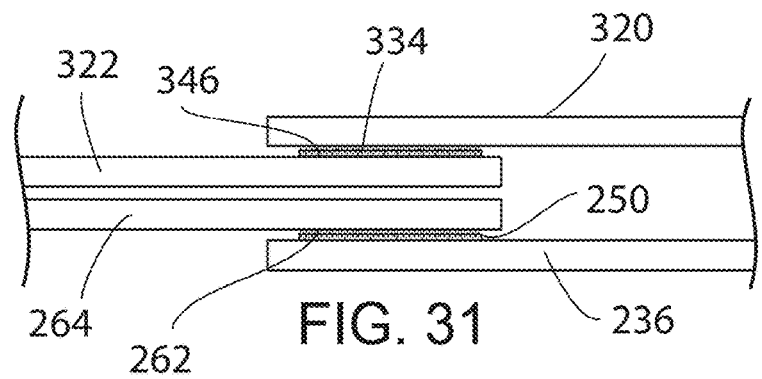
FIG. 31 illustrates a simplified side elevation view of the inventive predictive double-release alarm belt where first, second, third, and fourth elongated straps are attached to one another.
Figure 32:
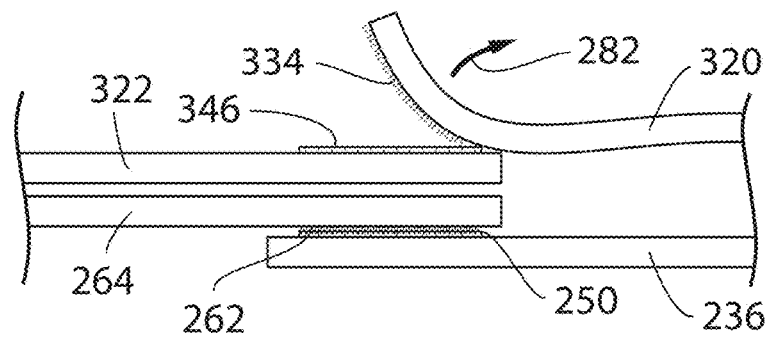
FIG. 32 illustrates a simplified side elevation view of the inventive predictive double-release alarm belt where the first elongated strap is being pulled in a first direction away from the second elongated strap to separate the first fastener from the fourth fastener.
Figure 33:
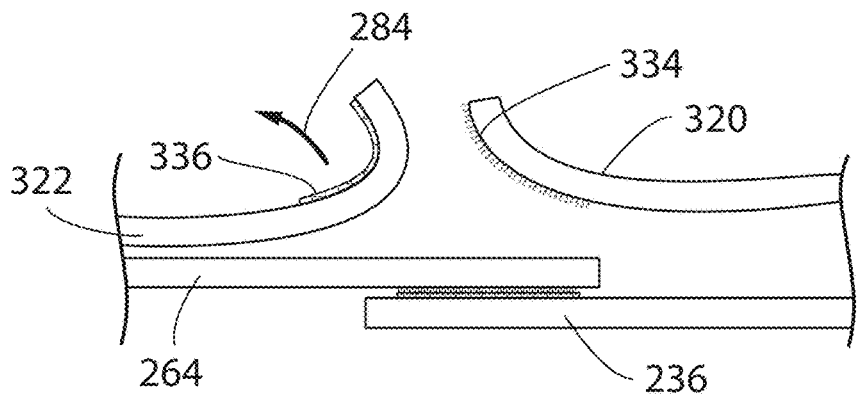
FIG. 33 illustrates a simplified side elevation view of the inventive predictive double-release belt where the second elongated strap is moved away from the third elongated strap and the fourth elongated strap.
Figure 34:
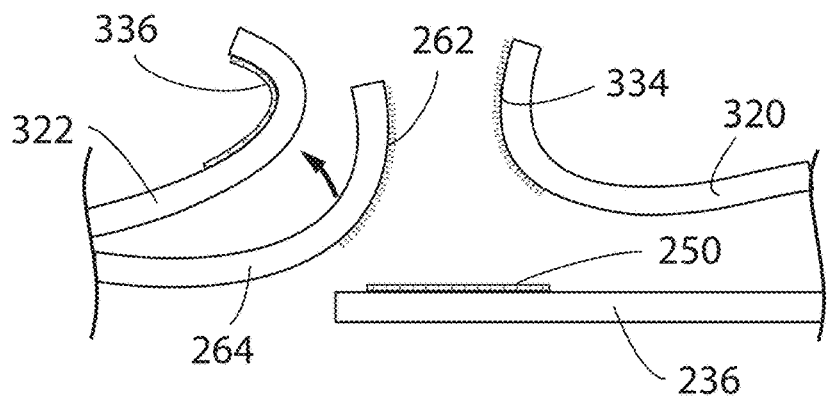
FIG. 34 illustrates a simplified side elevation view of the inventive predictive double-release alarm belt where the third elongated strap is being pulled in a second direction away from the fourth elongated strap to separate the second fastener from the third fastener.
Figure 35:
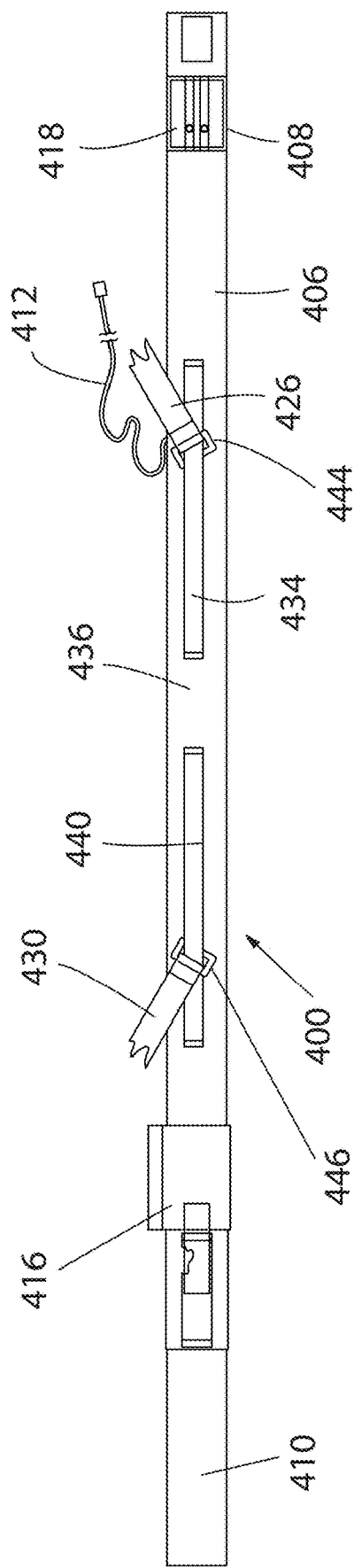
FIG. 35 illustrates a front side elevation view of an inventive integrated belt and sensor for alarm for patient furniture of the present invention.
Figure 36:
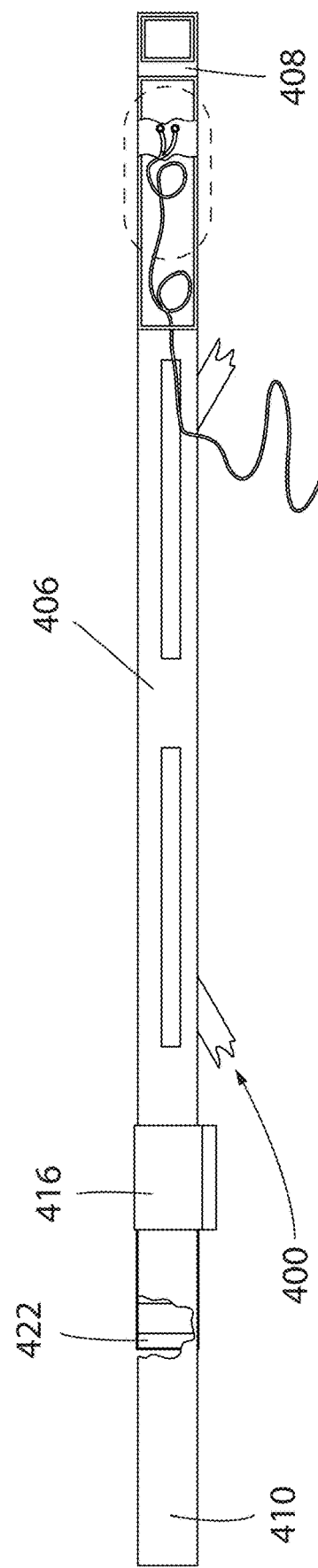
FIG. 36 illustrates a rear side elevation view of the inventive integrated belt and sensor for alarm for patient furniture of FIG. 35.
Figure 37:
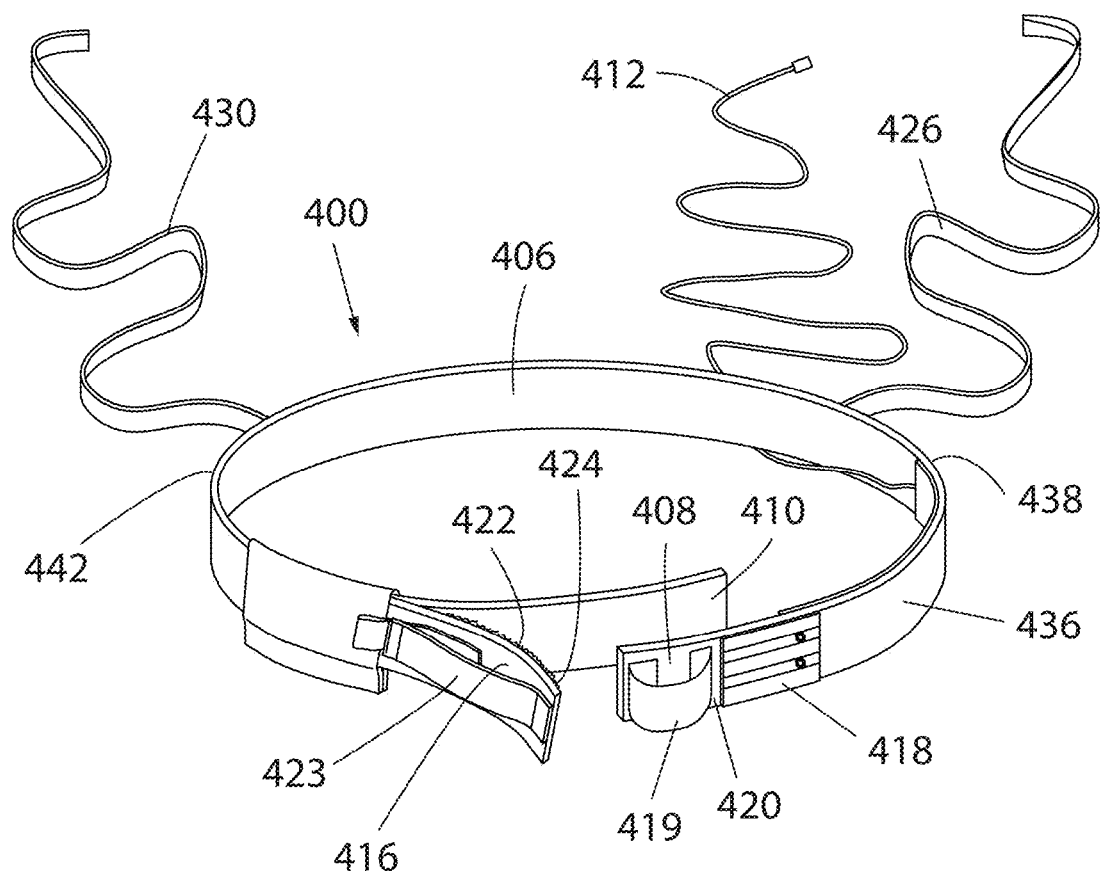
FIG. 37 illustrates an isometric view of the inventive integrated belt and sensor for alarm for patient furniture of FIGS. 35 and 36 in a partially assembled configuration.
Figure 38:
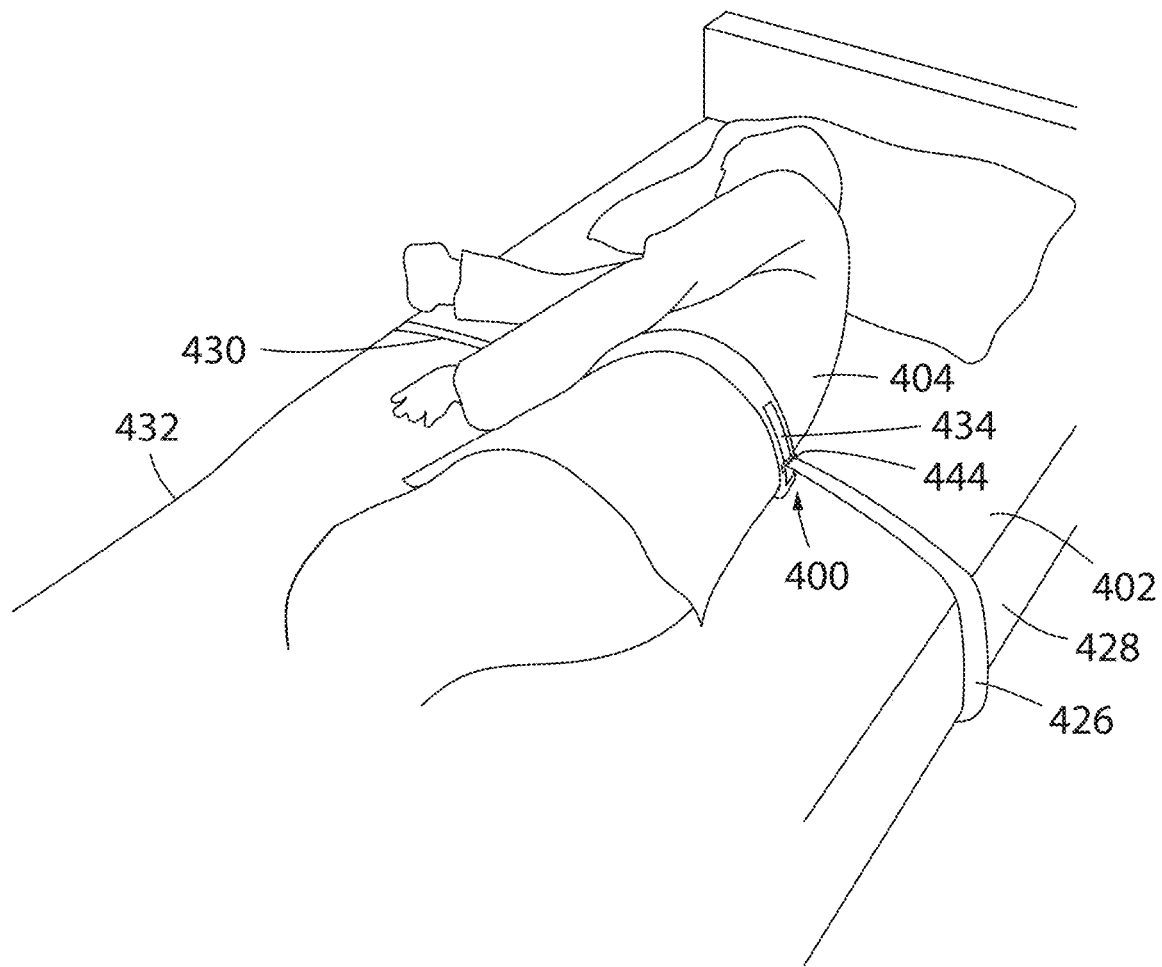
FIG. 38 illustrates an isometric view of the inventive integrated belt and sensor for alarm for patient furniture of FIGS. 35-37 in use with a patient.
Figure 41:
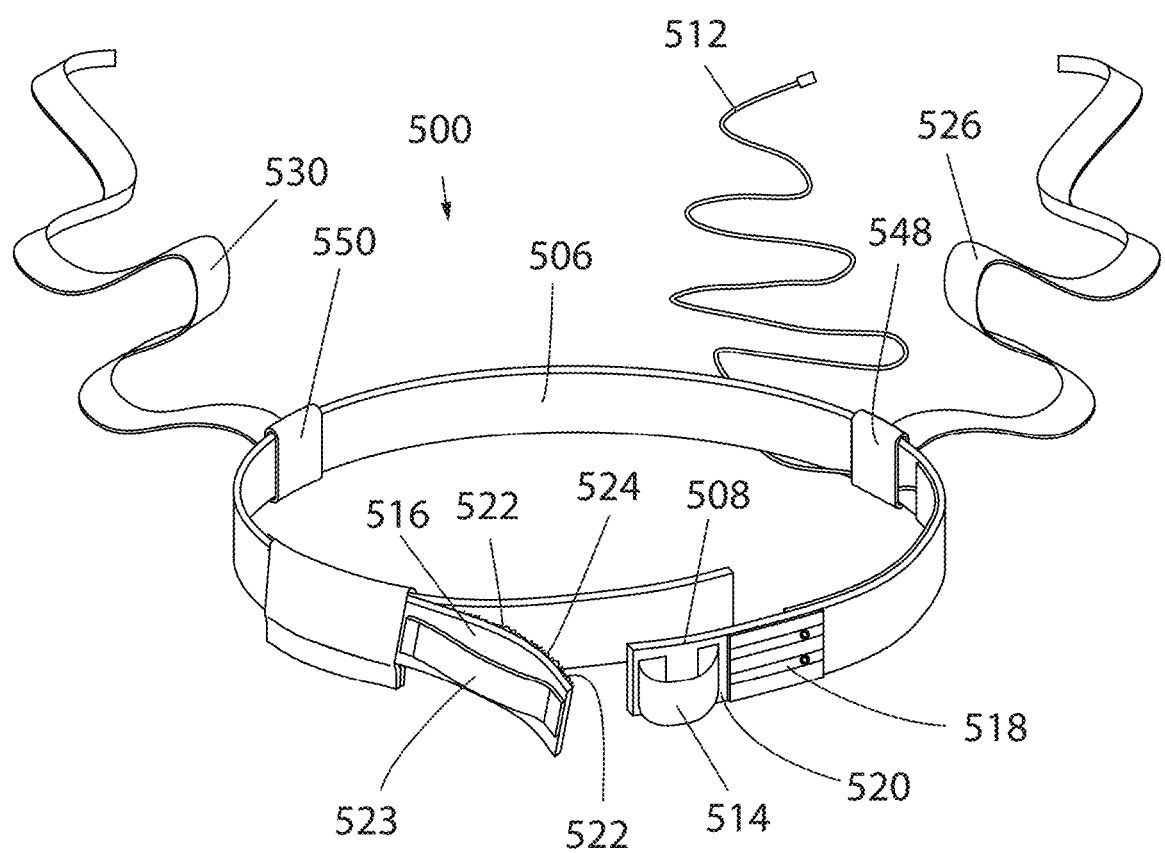
FIG. 41 illustrates an isometric view of the inventive integrated belt and sensor for alarm for patient furniture of FIGS. 39 and 40 in a partially assembled configuration.
Figure 42:
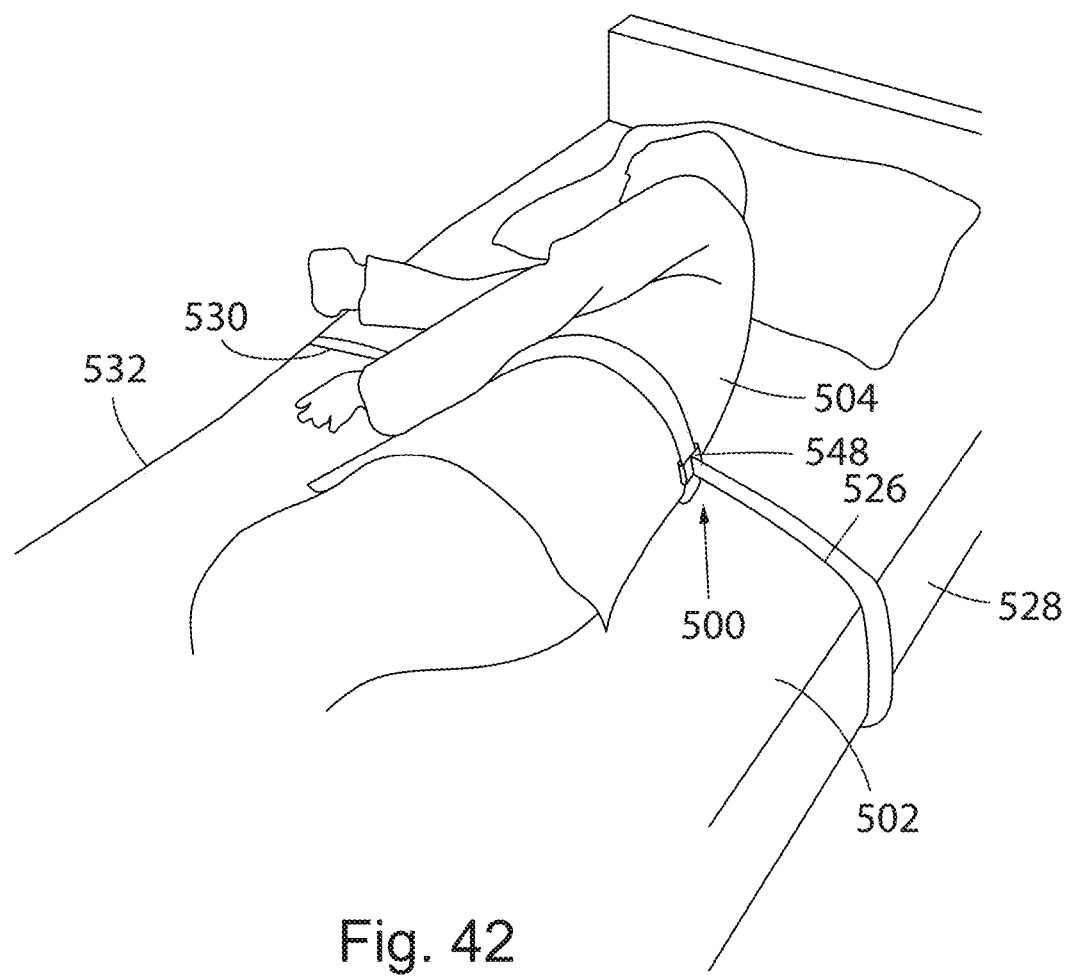
FIG. 42 illustrates an isometric view of the inventive integrated belt and sensor for alarm for patient furniture of FIGS. 39-41 in use with a patient.
Figure 45:
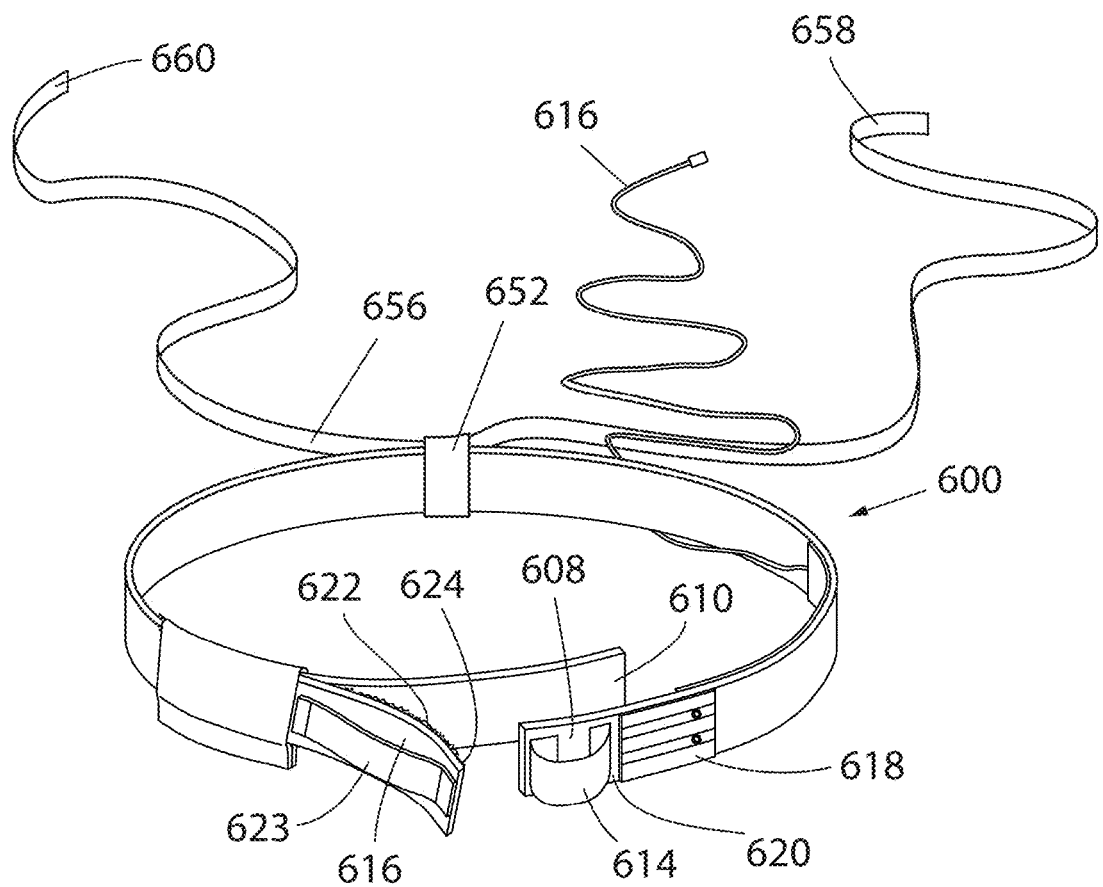
FIG. 45 illustrates an isometric view of the inventive integrated belt and sensor for alarm for patient furniture of FIGS. 43 and 44 in a partially assembled configuration.
Figure 46:
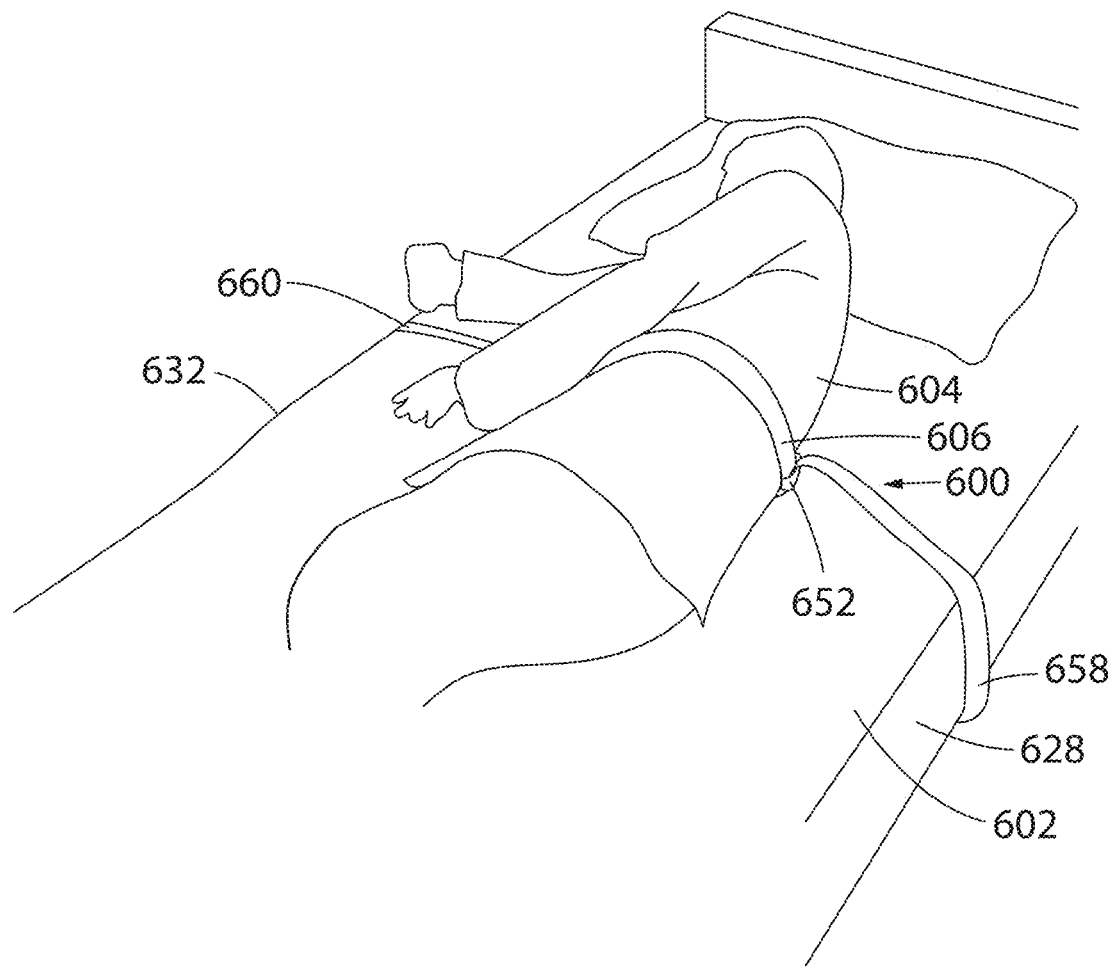
FIG. 46 illustrates an isometric view of the inventive integrated belt and sensor for alarm for patient furniture of FIGS. 43-45 in use with a patient.

Installation of the belt will now be described. First, the first and second ends of the base are secured to the device 232 as shown in FIG. 28. Next, the patient 234 is rested on the middle portion 352. Thereafter, the elongated straps are installed. Initially, the first elongated strap 236 is placed directly onto the patient 234. Thereafter, the second elongated strap 264 is placed on top of the first elongated strap 236. When this occurs, the first fastener 250 and the second fastener 262 make contact with one another and are fastened to one another. Next, the fourth elongated strap 322 is placed on top of the second elongated strap 264. Finally, the third elongated strap 320 is placed on top of the fourth elongated strap 322 such that the third fastener 334 and the fourth fastener 346 contact one another and are fastened together. Once this is complete, the double-release alarm belt 230 is secured in place as seen in FIG. 30.

As described above, once the third fastener 334 and the fourth fastener 346 are pulled apart by a first force 302, the alarm will sound to notify medical personnel that the patient 234 is trying to get out of the device 232 as described above. Next, the first fastener 250 and the second fastener 262 are pulled apart with a second force 304, such that the bond 300 between these fasteners 250, 262 is interrupted. The first force 302 required to disengage the third fastener 334 and the fourth fastener 346 is less than the second force 304 required to disengage the first fastener 250 and the second fastener 262. Preferably, the separation of the third and fourth fasteners 334, 346 occurs by pulling the second handle 288 in a first direction 282 and the separation of the first and second fasteners 250, 256 occurs by pulling the first handle 286 in a second direction 284 opposite the first direction 282. This results in increased time and difficulty for the patient 234 to remove the double-release alarm belt 30 than if the patient 34 simply had to repeatedly pull two separate belts in the same direction.

Furthermore, the bond (not shown) between the third fastener 334 and the fourth fastener 346 can be weaker than the bond (not shown) between the first fastener 250 and the second fastener 262. In this way, the patient 34 can more easily disengage the third fastener 334 and the fourth fastener 346, at which time the alarm will be sounded. Thereafter, due to the stronger bond between the first fastener 250 and the second fastener 262, it will be more difficult for the patient 234 to disengage these fasteners 250, 262. This makes it more difficult for the second bond to be broken, which increases the amount of time that medical staff has to approach the patient 234 after the initial alarm has been sounded. In this way, potential falls of the patient can be minimized.

FIGS. 35-38 show an inventive integrated belt and sensor system 400. The system 400 is configured for use with a device 402 on which a patient 404 is placed. For instance, as shown, the device 402 is a bed on which the patient 404 can lay. The system 400 is configured to allow for side-to-side movement of the patient 404 relative to the device 402 for added comfort, as will further be described below. The system 400 includes at least one strap, as shown, a first elongated strap 406 having a first end 408 and a second end 410. The system 400 also includes a cord 412 extending therefrom that is configured to detect movement of the first end 408 relative to the second end 410. The cord 412 is connected to an alarm system 414 that can be set off when the first end 408 is moved away from the second end 410. Thus, when a patient 404 is separating the first end 408 from the second end 410, which would need to occur before the patient 404 can exit the device 402, the alarm system 414 can be set off.

Additionally, as shown, the at least one strap also includes a second shortened strap 416. In the illustrated embodiment, the second shortened strap 416 is slidable relative to the first elongated strap 406. More specifically, the second shortened strap 416 is slidable relative to the second end 410 of the first elongated strap 406. In light of this slidable configuration, the second shortened strap 416 can be moved to alter the dimensions of the system 400. This allows a single system 400 to be used with a variety of different patients. For instance, if the patient 404 is smaller, the second shortened strap 416 can be slid away from the second end 410 such that the width of the system is smaller. To the contrary, where the patient 404 is larger, the second shortened strap 416 can be slid until it is directly next to the second end 410. Furthermore, the system 400 may be configured such that at least a portion of the second shortened strap 416 may be slid past the second end 410. In this way, the system 400 can quickly and easily be adjusted such that it is compatible with a wide variety of patients.

The first elongated strap 406 and the second shortened strap 416 may have various fasteners that allow for temporary, but removable connection between the straps. More specifically, the first elongated strap 406 may have a first fastener 418 located on an upper side 420 for the first end 408. The second shortened strap 416 may have a second fastener 422 mounted to an underside 424. Additionally, the second shortened strap 416 may also include a first handle 423. In such an embodiment, where the second shortened strap 416 is pulled away from the first end 408, for instance using the first handle 423, the connection between the first fastener 418 and the second fastener 422 can be broken. When this occurs, the alarm 414 can be sounded. As described above with regard to the other embodiments, the system 400 may also feature additional fasteners to enable the double-release alarm belt. For instance, additional fasteners (not shown), may be used to connect an underside of the first end 408 to the upper side of the second end 410. This would require a user to first disengage the second shortened strap 416 from the first elongated strap 406, after which the first end 408 and the second end 410 can be disengaged from one another. Because the alarm 414 is sounded based on the initial separation of the second shortened strap 416 from the first elongated strap 406, a caregiver will have time to check on the patient 404 while the second disengagement is occurring. The first elongated strap 406 may include a second handle 419 that can be used to more easily separate the first end 408 from the second end 410.

Additionally, the system 400 may have multiple securement straps configured to secure the system 400 to the device 402. Still looking to FIGS. 35-38, as shown, this embodiment includes a first securement strap 426 and a second securement strap 430. The first securement strap 426 is configured to extend from the first elongated strap 406 to a first side 428 of the device 402, and the second securement strap 430 is configured to extend from the first elongated strap 406 to a second side 432 of the device 402. The straps 426, 430 can be affixed to either side 428, 432 using any suitable means, including hook-and-loop fasteners, snaps, hooks, and any other fastener known in the art. Additionally, as shown, this embodiment includes a first track 434 mounted to an outer side 436 of the first elongated strap 406 at a first end 438, and a second track 440 mounted to the outer side 436 of the first elongated strap 406 at a second end 442. The tracks 434, 440 are configured to be compatible with hoops that can travel along the length of the tracks 434, 440. A first hoop 444 can move along the first track 434, and a second hoop 446 can move along the second track 440. The first securement strap 426 is attached to the first hoop 444 and the second securement strap 430 is attached to the second hoop 446.

As a result of the slidable relationship of the hoops 444, 446 relative to the tracks 434, 440, a patient roll concept is achieved that allows a patient 404 to have greater movement while being safely secured and having two releasing points. This allows a patient 404 to easily and comfortably move side-to-side relative to the device 402. This helps to ensure comfort of the patient 404 while they are in the device 402 and can help to reduce bed sores that can occur where the patient 404 remains in the same position on the device 402 for extended periods of time. The system 400 may even allow a patient 404 to comfortably sit up without disengaging the straps.

Another embodiment is shown in FIGS. 39-42. Many of the components in this embodiment are similar to those shown in FIGS. 35-38. Those that are similar to the components found in FIGS. 35-38 will be designated by the same reference numbers as those provided above incremented by 100. In addition, the system 500 includes a first slider 548 and a second slider 550. The first securement strap 526 is attached to the first slider 548 and the second securement strap 530 is attached to the second slider 550. Instead of the tracks and hoops described above, these sliders 548, 550 slide relative to the first elongated strap 506 to enable side-to-side movement of the patient 404. The sliders 548, 550 can be made of any material, but preferably are made of a thin, comfortable material that a patient 504 can rest upon but would not get irritated by. Additionally, the material is preferably configured for optimal movement of the sliders 548, 550 relative to the first elongated strap 406 without causing the sliders 548, 550 to get caught or snagged on the first elongated strap 406.

Another embodiment is shown in FIGS. 43-46. Many of the components in this embodiment are similar to those shown in FIGS. 35-38. Those that are similar to the components found in FIGS. 35-38 will be designated by the same reference numbers as those provided above incremented by 200. In addition, the system 600 includes a loop 652 mounted to the back side 654 of the first elongated strap 606. The loop 652 may be made of a soft, flexible material such that it does not cause discomfort to the patient 604 if the patient 604 lies directedly on the loop 652. The loop 652 may be slidable relative to the first elongated strap 606 so that the patient 604 can move the first elongated strap 606 relative to the device 602. Alternatively, the loop 652 may be fixedly attached to the first elongated strap 606. Whether or not the loop 652 is fixed or slidable relative to the first elongated strap 602 may be dependent on the amount of side-to-side movement desired for a given patient. Additionally, the system 600 includes a single securement strap 656. The single securement strap 656 has a first end 658 and a second end 660. The single securement strap 656 is attached to the first side 628 of the device 602 and the second end 660 is attached to the second side 642 of the device. Again, this enables the patient 604 to move side-to-side relative to the device 602 to help improve comfort when the patient 604 is resting on the device 602.

Figure 47:
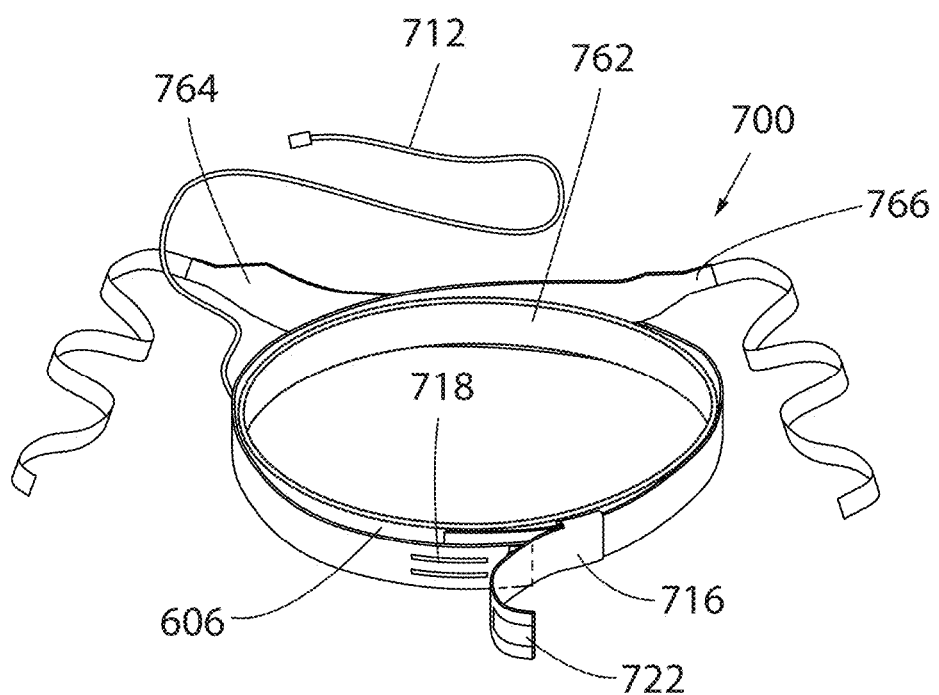
FIG. 47 illustrates an isometric view of an inventive integrated belt and sensor for alarm for patient furniture in a partially assembled configuration.
Figure 48:
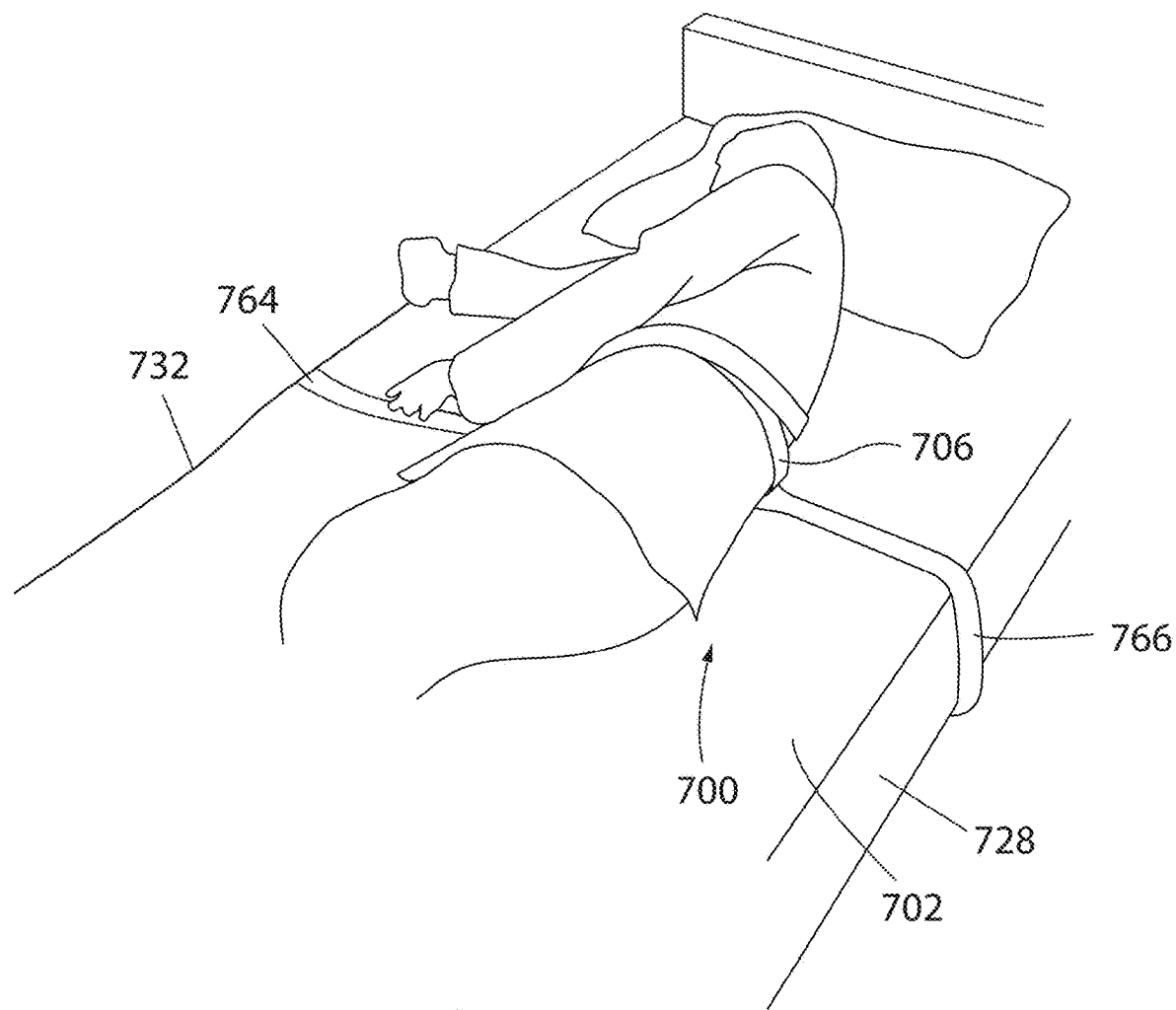
FIG. 48 illustrates an isometric view of the inventive integrated belt and sensor for alarm for patient furniture of FIG. 47 in use with a patient.

Yet another embodiment is shown in FIGS. 47-48. Many of the components in this embodiment are similar to those shown in FIGS. 35-38. Those that are similar to the components found in FIGS. 35-38 will be designated by the same reference numbers as those provided above incremented by 300. In addition to the components described above, the system 700 additionally includes a first securement strap 764 extending from the first end 738 and a second securement strap 766 extending from the second end 742. As shown, the first securement strap 764 and the second securement strap 766 are fixedly attached to the first elongated strap 706. However, the first securement strap 764 and the second securement strap 766 could also be affixed to sliders (not shown) similar to those shown in FIGS. 39-42, which would enable the sliders, and by extension the securement straps 764, 766, to be adjusted and movable relative to the first elongated strap 706. The first securement strap 764 and the second securement strap 766 are configured to criss-cross behind the patient 704. As such, the first securement strap 764 is attached to the second side 732 of the device 702, whereas the second securement strap 766 is attached to the first side 728 of the device 702. As a result of the criss-cross configuration of the straps 764, 766 and the length of the straps 764, 766, the patient 704 can move side-to-side relative to the device 702 for added comfort when the patient 704 is resting on the device 702. Additionally, the system 700 may include a cover (not shown) mounted to the back of the first elongated strap 706 to cover the criss-crossing first securement strap 426 and the second securement strap 430. Such a cover is beneficial in that it helps to ensure that the straps 426, 430 are properly crossing one another. This is important because the crossing of the straps 426, 430 helps to enable the side-to-side movement of the patient.

Figure 49:
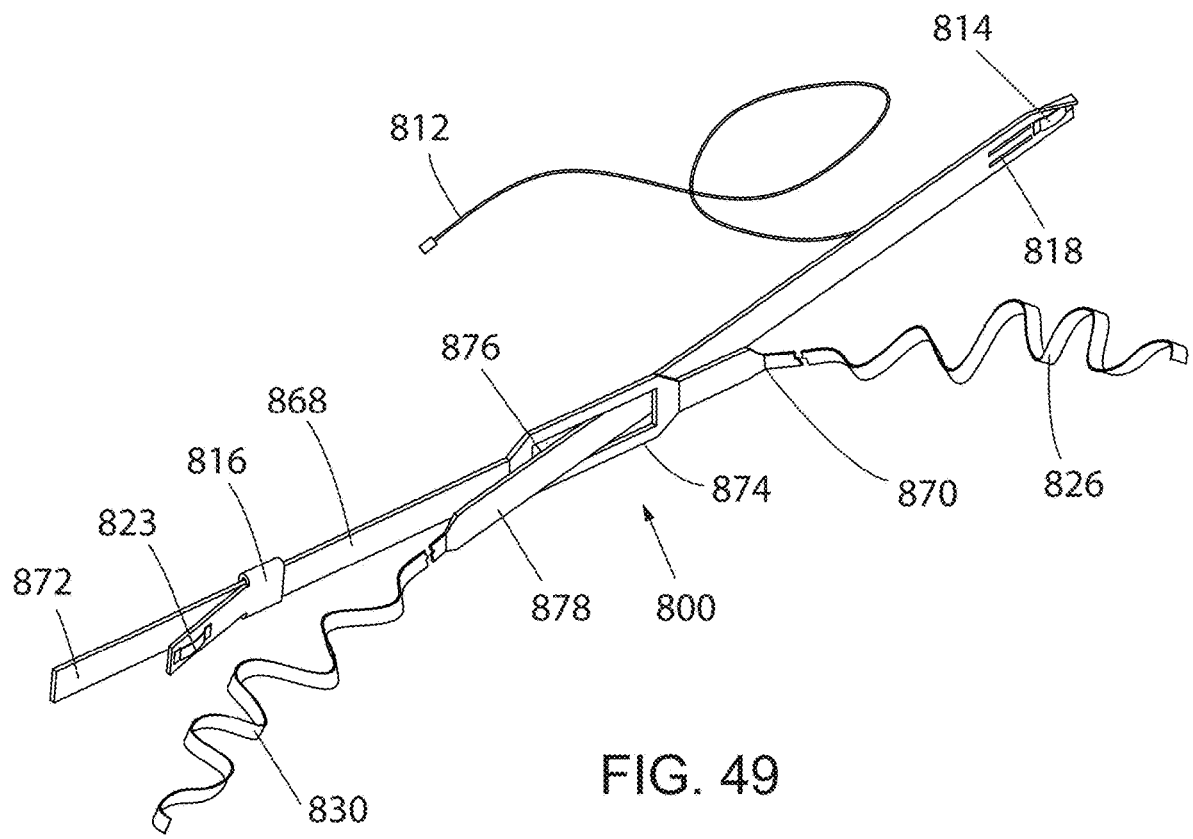
FIG. 49 illustrates an isometric view of an inventive integrated belt and sensor for alarm for patient furniture in an unassembled configuration.
Figure 50:
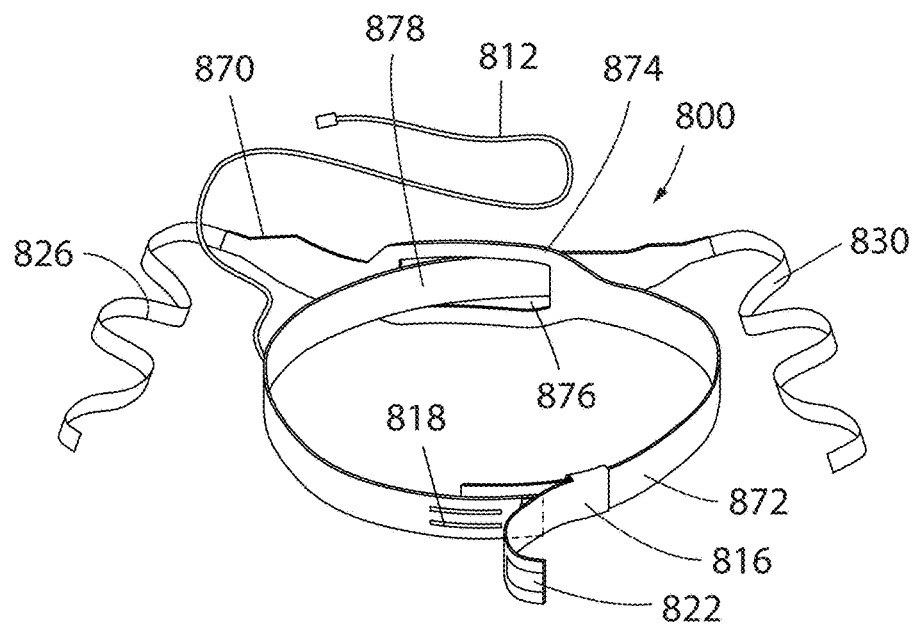
FIG. 50 illustrates an isometric view of the inventive integrated belt and sensor for alarm for patient furniture of FIG. 49 in a partially assembled configuration.
Figure 51:
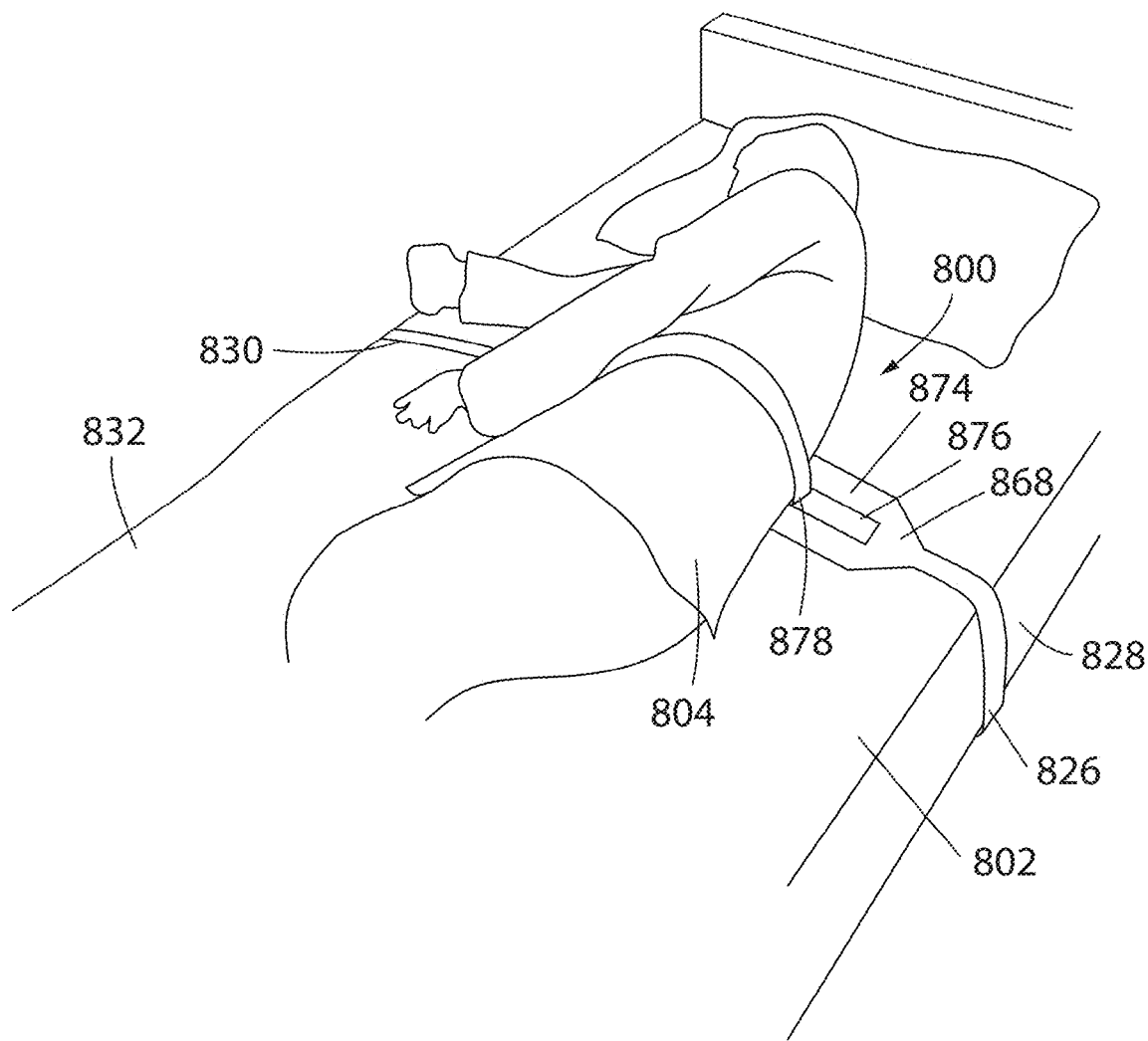
FIG. 51 illustrates an isometric view of the inventive integrated belt and sensor for alarm for patient furniture of FIGS. 49 and 50 in use with a patient.

Turning next to FIGS. 49-51, another embodiment is shown. Many of the components in this embodiment are similar to those shown in FIGS. 35-38. Those that are similar to the components found in FIGS. 35-38 will be designated by the same reference numbers as those provided above incremented by 400. In this embodiment, the system 800 includes a first elongated strap 868 and a second elongated strap 878. The first elongated strap 868 has a first end 870, a second end 872, and a middle portion 874 located between the first end 870 and the second end 872. An opening 876 is formed in the middle portion 874 through which the second elongated strap 878 can be threaded. As shown, the first securement strap 826 extends from the first elongated strap 868 and the second securement strap 830 extends form the second elongated strap 878. As a result of the opening 876 and the orientation of the second elongated strap 878 relating thereto, side-to-side movement of the patient is enabled.

All of the systems described above can be used in similar ways to enable health care professionals to monitor a patient's location relative to the device, and more importantly, to sound an alarm when a patient begins to disengage the system before he or she can get up from the device. Steps associated with a method of using the system will now be described. Initially, at least one strap is wrapped around the patient. Once this occurs, a first end and a second end of the strap are engaged with one another. Once the ends are engaged, an alarm system may be connected to the alarm system. From here, at least one securement strap that extends from the patient strap can be secured to a side of the device. The relationship of the patient strap and the securement strap allows the patient to move side-to-side relative to the device for added comfort.

The method may also include use of additional components to enable this side-to-side movement. For instance, the system may include a track or tracks and hooks that can slide along the track. As such, the system may include a first track on a first side of the patient strap and a second track on a second side of the patient strap. In such an embodiment, hooks travel along the length of the track, and securement straps extend from the hooks to enable side-to-side movement. Alternatively, the system may include at least one adjustable slider that has a securement strap extending therefrom to also enable side-to-side movement. Further still, the system may include a loop with a securement strap that extends therethrough.

In any of these embodiments, the system may also include multiple releases. For instance, the system may include a first release mechanism and a second release mechanism. When the first release mechanism is released, an alarm can be sounded. At this time, the patient is still seated or lying on the device. It is not until the second release mechanism is released that the patient can get up and exit the device.

All the disclosed embodiments are useful in conjunction with patient monitoring. There are virtually innumerable uses for the present invention, all of which need not be detailed here. All the disclosed embodiments can be practiced without undue experimentation.

Although the best mode contemplated by the inventors of carrying out the present invention is disclosed above, practice of the present invention is not limited thereto. It will be manifest that various additions, modifications, and rearrangements of the features of the present invention may be made without deviating from the spirit and scope of the underlying inventive concept.

For example, additional elongated straps or shortened straps could be used in conjunction with the straps described above. Similarly, additional fasteners could also be used to increase the amount of time between when the patient begins to remove the belt and when the patient is able to get up from the device. Also, the fasteners need not be in the exact locations described but could be located anywhere about the various straps. In addition, the individual components need not be fabricated from the disclosed materials but could be fabricated from virtually any suitable materials.

Moreover, the individual components need not be formed in the disclosed shapes, or assembled in the disclosed configuration, but could be provided in virtually any shape and assembled in virtually any configuration. Furthermore, all the disclosed features of each disclosed embodiment can be combined with, or substituted for, the disclosed features of every other disclosed embodiment except where such features are mutually exclusive.

It is intended that the appended claims cover all such additions, modifications, and rearrangements. Expedient embodiments of the present invention are differentiated by the appended claims.

What is claimed is:

1. An integrated belt and sensor for alarm system for use with a device holding a patient comprising:
   at least one strap having a first end and a second end, the second end releasably secured to the first end around the patient;
   a cord configured to detect movement of the first end relative to the second end; and
   an alarm system connected to the cord;
   wherein the alarm system is activated when the first end and the second end are separated.

2. The integrated belt and sensor for alarm system of claim 1, wherein the at least one strap further comprises:
   a first elongated strap; and
   a second shortened strap configured to be releasably attached to the first elongated strap;
   wherein the second shortened strap is disengaged from the first elongated strap by pulling the second shortened strap in a first direction; and
   wherein the alarm system is triggered when the second shortened strap is disengaged from the first elongated strap.

3. The integrated belt and sensor for alarm system of claim 2, wherein the second shortened strap is slidably adjustable relative to the first elongated strap.

4. The integrated belt and sensor for alarm system of claim 2, further comprising:
a first fastener on an upper side of the first elongated strap; and
a second fastener on an underside of the second shortened strap;
wherein the second fastener is configured to releasably fasten to the first fastener; and
wherein the alarm system is triggered when the first fastener is separated from the second fastener.

5. The integrated belt and sensor for alarm system of claim 4, further comprising:
a first securement strap extending from the first elongated strap that is configured to be secured to a first side of the device; and
a second securement strap extending from the first elongated strap that is configured to be secured to a second side of the device.

6. The integrated belt and sensor for alarm system of claim 5, further comprising:
a first track mounted to an outer side of the first elongated strap at a first end;
a second track mounted to the outer side of the first elongated strap at a second end;
a first hoop mounted to the first securement strap, wherein the first hoop travels along the first track; and
a second hoop mounted to the second securements trap, wherein the second hoop travels along the second track;
wherein the first track, first hoop, second track, and second hoop enable side-to-side movement of the patient relative to the device.

7. The integrated belt and sensor for alarm system of claim 5, further comprising:
a first slider wrapped around a first end of the first elongated strap; and
a second slider wrapped around a second end of the first elongated strap;
wherein the first slider is configured for slidable movement along the first end;
wherein the second slider is configured for slidable movement along the second end;
wherein the first securement strap is connected to the first slider;
wherein the second securement strap is connected to the second slider;
wherein the first slider and the second slider enable side-to-side movement of the patient relative to the device.

8. The integrated belt and sensor for alarm system of claim 2, further comprising:
a loop mounted to a back side of the first elongated strap; and
a securement strap having a first end and a second end;
wherein the first end is attached to a first end of the device;
wherein the second end is attached to a second end of the device;
wherein the securement strap is threaded through the loop to enable side-to-side movement of the patient relative to the device.

9. The integrated belt and sensor for alarm system of claim 1 wherein:
the at least one strap further comprises:
a first strap affixed around a body of the patient;
a second securement strap extending from a first side of the first strap;
a third securement strap extending from a second side of the first strap;
wherein the third securement strap wraps around the back side of the patient to a second side of the device;
wherein the second securement strap and the third securement strap cross one another behind the back of the patient to enable side-to-side movement of the patient relative to the device.

10. The integrated belt and sensor for alarm system of claim 1 wherein:
the at least one strap further comprises:
a first elongated strap comprising:
a first end,
a second end,
a middle portion located between the first end and the second end, and
an opening formed in the middle portion; and
a second elongated strap that extends through the opening formed in the first elongated strap;
wherein the second elongated strap is movable relative to the first elongated strap about the opening to enable side-to-side movement of the patient relative to the device.

11. The integrated belt and sensor for alarm system of claim 1 wherein:
the at least one strap further comprises:
a first elongated strap;
a second elongated strap configured to be releasably attached to the first elongated strap;
wherein the second elongated strap is disengaged from the first elongated strap by pulling the first elongated strap in a first direction; and
wherein the alarm system is triggered when the second elongated strap is disengaged from the first elongated strap.

12. An integrated belt and sensor for alarm system for use with a device holding a patient comprising:
at least two straps releasably secured to one another;
a cord configured to detect movement of at least one of the straps; and
an alarm system connected to the cord;
wherein the alarm system is activated when at least one of the straps is moved relative to the other strap.

13. The integrated belt and sensor for alarm system of claim 12, wherein the at least two straps further comprise:
a first elongated strap;
a second shortened strap configured to be releasably attached to the first elongated strap;
a first fastener on an upper side of the first elongated strap;
a second fastener on an underside of the second shortened strap, wherein the second fastener is configured to releasably fasten to the first fastener;
wherein the alarm system is triggered when the first fastener is separated from the second fastener.

14. The integrated belt and sensor for alarm system of claim 13, further comprising:
at least one securement strap extending from one of the at least two straps that enable side-to-side movement of the patient relative to the device.

15. The integrated belt and sensor for alarm system of claim 12, wherein the at least two straps further comprise:
at least one strap wrapped around the patient; and
at least two securement straps extending from opposite ends of the at least one strap wrapped around the patient;

wherein the at least two securement straps are connected to opposite ends of the device; and wherein the at least two securement straps enable side-to-side movement of the patient relative to the device.

16. A method of using an integrated belt and sensor for alarm system for use with a device holding a patient comprising the steps of:

wrapping at least one strap temporarily around the patient;

engaging a first end of the at least one strap with a second end of the at least one strap;

connecting an alarm system to the at least one strap;

securing at least one securement strap that extends from the at least one patient strap to a side of the device; and enabling side-to-side movement of the patient relative to the device.

17. The method of claim 16, further comprising the steps of:

sliding a first hook that is attached to the first securement strap along a first track located on a first side of the at least one patient strap; and sliding a second hook that is attached to the second securement strap along a second track located on a second side of the at least one patient strap.

18. The method of claim 16, further comprising the steps of:

sliding a first slider that is attached to the first securement strap, where the first slider wraps around a first side of the at least one patient strap along the at least one patient strap; and sliding a second slider that is attached to the second securements strap, where the second slider wraps around a second side of the at least one patient strap along the at least one patient strap.

19. The method of claim 16, further comprising the steps of:

disengaging the first end from the second end;

enabling the alarm system to create an audible alarm; and then further disengaging the at least one strap to enable the patient to exit the device.

\* \* \* \* \*